(12) United States Patent
Olson et al.

(10) Patent No.: US 6,924,415 B2
(45) Date of Patent: Aug. 2, 2005

(54) TRANSGENIC MICE COMPRISING A CONSTITUTIVELY-ACTIVATED MEK5 AND EXHIBITING CARDIAC HYPERTROPHY AND DILATED CARDIOMYOPATHY

(75) Inventors: Eric N. Olson, Dallas, TX (US); Rebekka Nicol, Hicksville, NY (US)

(73) Assignee: Board of Regents, The University of Texas System, Austin, TX (US)

( * ) Notice: Subject to any disclaimer, the term of this patent is extended or adjusted under 35 U.S.C. 154(b) by 106 days.

(21) Appl. No.: 10/159,971

(22) Filed: May 30, 2002

(65) Prior Publication Data

US 2003/0144176 A1 Jul. 31, 2003

Related U.S. Application Data

(60) Provisional application No. 60/295,875, filed on Jun. 4, 2001.

(51) Int. Cl.$^7$ ..................... A01K 67/00; A01K 67/033; A01K 67/027; C12N 5/06; C12N 5/16

(52) U.S. Cl. ................................ 800/18; 800/8; 800/9; 800/13; 800/14; 800/21; 435/325; 435/354; 435/235

(58) Field of Search ................................ 800/8, 18, 21; 435/325, 354, 235

(56) References Cited

U.S. PATENT DOCUMENTS 6,046,381 A * 4/2000 Mucke et al. .................. 800/18

OTHER PUBLICATIONS

Nicol, et al. (2001) EMBO J., 20(11):2757–67.*
Mullins, et al. (1996) J. Clin. Invest. 98(11 Suppl.): S37–S40.*
Cameron (1997) Molec. Biotechnol., 7: 253–65.*
Sigmund (2000) Artioscler. Thromb. Vasc. Biol., 20: 1425–29.*
Neimann (1998) Transg. Res., 7: 73–75.*
Kappel, et al. (1992) Curr. Opin. Biotech., 3: 548–53.*
Mullins, et al. (1993) Hypertension, 22: 630–33.*
Houdebine (1994) J. Biotechnol., 34: 269–87.*
Wall (1996) Theriogenology, 45: 57–68.*
Abe et al., "Big mitogen–activated protein kinase 1 (BMK1) is redox–sensitive kinase," *J. Biol. Chem.*, 271:16586–16590, 1996.
Abe et al., "Role of mitogen–activated protein kinases in ischemia and reperfusion injury. The good and the bad," *Cir. Res.*, 86:607–609, 2000.
Adams et al., "Enhanced Gαq signaling: a common pathway mediates cardiac hypertrophy and apoptotic heart failure," *Proc. Nat'l Acad. Sci. USA*, 95:10140–10145, 1998.
Bueno et al., "The dual–specificity phosphatase MKP–1 limits the cardiac hypertrophic response in vitro and in vivo," *Circ. Res.*, 88:88–96, 2001.
Bueno et al., "The MEK1–ERK 1/2 signaling pathway promotes compensated cardiac hypertrophy in transgenic mice," *EMBO J.*, 19:6341–6350, 2000.

Chien, "Stress pathways and heart failure," *Cell*, 98:555–558, 1999.
English et al., "Contribution of the ERK5/MEK5 pathway to Ras/Raf signaling and growth control," *J. Biol. Chem.*, 274:31588–31592, 1999.
English et al., "Isolation of MEK5 and differential expression of alternatively spliced forms," *J. Biol. Chem.*, 270(48):28897–28902, 1995.
English et al., "New insights into the control of MAP kinase pathways," *Exper. Cell Res.*, 253:255–270, 1999.
Frey et al., "Decoding calcium signals involved in cardiac growth and function," *Nature Med.*, 6:1221–1227, 2000.
Fukuhara et al., "Signaling from G protein–coupled receptors to ERK5/big MAPK 1 involves $G\alpha_q$ and $G\alpha_{12/13}$ families of heterotrimeric G proteins," *J. Biol. Chem.*, 275:21730–21736, 2000.
Ikeda and Ross, "Models of dilated cardiomyopathy in the mouse and the hamster," *Curr. Opin. Card.*, 15:197–201, 2000.
Kamakura et al., "Activation of the protein kinase ERK5/MBK1 receptor tyrosine kinases," *J. Biol. Chem.*, 274:26563–26571, 1999.
Kasler et al., "ERK5 is a novel type of mitogen–activated protein kinase containing a transcriptional activation domain," *Mol. Cell. Biol.*, 20:8382–8389, 2000.
Kato et al., "BMK1/ERK5 regulates serum–induced early gene expression through transcription factor MEF2C," *EMBO J.*, 16(2 3):7054–7066, 1997.
Lee et al., "Primary structure of MBK1: a new mammalian MAP kinase," *Bioch & Biophys. Res. Comm.*, 213:715–724, 1995.
MacLellan and Schneider, "Genetic dissection of cardiac growth control pathways," *Annu. Rev. Physiol.*, 62:289–319, 2000.
MacLellan and Schneider, "Programmed cell death in cardiovascular biology and disease," *Circ. Res.*, 81:137–144, 1997.
Molkentin et al., "A calcineurin–dependent transcriptional pathway for cardiac hypertrophy," *Cell*, 93:215–228, 1998.

*Primary Examiner*—Anne M. Wehbe
*Assistant Examiner*—Robert M. Kelly
(74) *Attorney, Agent, or Firm*—Fulbright & Jaworski, LLP

(57) ABSTRACT

The present invention relates to compositions and methods relating to MEK5 and its role in heart disease. This protein has now been identified as a target for therapeutic intervention due to its role molecular events that lead to or contribute to cardiac hypertrophy and/or dilated cardiomyopathy. In particular, inhibition of MEK5 activity will lead to decrease signalling of the pathways and reduce or eliminate the effects on sarcomere assembly, which in turn result or contribute to cardiac dysfunction. Also provided are transgenic animals and methods of screening for inhibitors of MEK5.

1 Claim, 10 Drawing Sheets

OTHER PUBLICATIONS

Nicol et al., "From the sarcomere to the nucleus: role of genetics and signaling in structural heart disease," *Ann. Rev. Gen. Gen.*, 1:179–223, 2000.

Passier et al., "CaM kinase signaling induces cardiac hypertrophy and activates the MEF2 transcription factor in vivo," *J. Clin. Invest.*, 105:1395–1406, 2000.

Ruwhof and van der Laarse, "Mechanical stress–induced cardiac hypertrophy: mechanism and signal transduction pathways," *Card. Res.*, 47:23–37, 2000.

Sugden and Clerk, "Cellular mechanisms of cardiac hypertrophy," *J. Mol. Med.*, 76:725–746, 1998.

Sugden and Clerk, "Stress–responsive mitogen–activated protein kinases (c–jun n–terminal kinases and p38 mitogen–activated protein kinases) in the myocardium," *Circ. Res.*, 83: 345–352, 1998.

Takeishi et al., "Differential regulation of p90 ribosomal S6 kinase and big mitogen–activated protein kinase 1 by ischemia/reperfusion and oxidative stress in perfused guinea pig hearts," *Circ. Res.*, 85:1164–1172, 1999.

Tamura et al., "Correlation of myocyte lengthening to chamber dilation in the spontaneously hypertensive heart failure (SHHF) rat," *J. Mol. & Cell. Card.*, 30:2175–2181, 1998.

Wang et al., "Cardiac hypertrophy induced by mitogen–activated protein kinase kinase 7, a specific activator for c–Jun $NH_2$–terminal kinase in ventricular muscle cells," *J. Biol. Chem.*, 273:5423–5426, 1998.

Wang et al., "Cardiac muscle cell hypertrophy and apoptosis induced by distinct members of the p38 mitogen–activated protein kinase family," *J. Biol. Chem.*, 273:2161–2168, 1998.

Zhang et al., "TAK1 is activated in the myocardium after pressure overload and is sufficient to provoke heart failure in transgenic mice," *Nat. Med.* 6:556–563, 2000.

Zhou et al., "Components of a new human protein kinase signal transduction pathway," *J. Biol. Chem.*, 270(21):12665–12669, 1995.

\* cited by examiner

A Immunoblot: anti-HA

← HA-MEK5DD

B Immunoblot: anti-MEK5

← MEK5β
*

C Immunoblot: anti-ERK5

← ERK5

SEQUENCE LISTING

<160> NUMBER OF SEQ ID NOS: 4
<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

```
Met Leu Trp Leu Ala Leu Gly Pro Phe Arg Ala Met Glu Asn Gln Val
 1               5                  10                  15

Leu Val Ile Arg Ile Lys Ile Pro Asn Ser Gly Ala Val Asp Trp Thr
             20                  25                  30

Val His Ser Gly Pro Gln Leu Leu Phe Arg Asp Val Leu Asp Val Ile
         35                  40                  45

Gly Gln Val Leu Pro Glu Ala Thr Thr Thr Ala Phe Glu Tyr Glu Asp
     50                  55                  60

Glu Asp Gly Asp Arg Ile Thr Val Arg Ser Asp Glu Glu Met Lys Ala
 65                  70                  75                  80

Met Leu Ser Tyr Tyr Tyr Ser Thr Val Met Glu Gln Gln Val Asn Gly
                 85                  90                  95

Gln Leu Ile Glu Pro Leu Gln Ile Phe Pro Arg Ala Cys Lys Pro Pro
            100                 105                 110

Gly Glu Arg Asn Ile His Gly Leu Lys Val Asn Thr Arg Ala Gly Pro
        115                 120                 125

Ser Gln His Thr Ser Pro Val Val Ser Asp Ser Leu Pro Ser Asn Ser
    130                 135                 140

Leu Lys Lys Ser Ser Ala Glu Leu Arg Lys Ile Leu Ala Asn Gly Gln
145                 150                 155                 160

Met Asn Glu Gln Asp Ile Arg Tyr Arg Asp Thr Leu Gly His Gly Asn
                165                 170                 175

Gly Gly Thr Val Tyr Lys Ala Tyr His Val Pro Ser Gly Lys Ile Leu
            180                 185                 190

Ala Val Lys Val Ile Leu Leu Asp Ile Thr Leu Glu Leu Gln Lys Gln
        195                 200                 205

Ile Met Ser Glu Leu Glu Ile Leu Tyr Lys Cys Asp Ser Ser Tyr Ile
    210                 215                 220

Ile Gly Phe Tyr Gly Ala Phe Phe Val Glu Asn Arg Ile Ser Ile Cys
225                 230                 235                 240

Thr Glu Phe Met Asp Gly Gly Ser Leu Asp Val Tyr Arg Lys Ile Pro
                245                 250                 255

Glu His Val Leu Gly Arg Ile Ala Val Ala Val Val Lys Gly Leu Thr
            260                 265                 270
```

```
Tyr Leu Trp Ser Leu Lys Ile Leu His Arg Asp Val Lys Pro Ser Asn
            275                 280                 285
Met Leu Val Asn Thr Ser Gly Gln Val Lys Leu Cys Asp Phe Gly Val
        290                 295                 300
Ser Thr Gln Leu Val Asn Ser Ile Ala Lys Thr Tyr Val Gly Thr Asn
305                 310                 315                 320
Ala Tyr Met Ala Pro Glu Arg Ile Ser Gly Glu Gln Tyr Gly Ile His
                325                 330                 335
Ser Asp Val Trp Ser Leu Gly Ile Ser Phe Met Glu Leu Ala Leu Gly
            340                 345                 350
Arg Phe Pro Tyr Pro Gln Ile Gln Lys Asn Gln Gly Ser Leu Met Pro
        355                 360                 365
Leu Gln Leu Leu Gln Cys Ile Val Asp Glu Asp Ser Pro Val Leu Pro
    370                 375                 380
Leu Gly Glu Phe Ser Glu Pro Phe Val His Phe Ile Thr Gln Cys Met
385                 390                 395                 400
Arg Lys Gln Pro Lys Glu Arg Pro Ala Pro Glu Glu Leu Met Gly His
                405                 410                 415
Pro Phe Ile Val Gln Phe Asn Asp Gly Asn Ala Thr Val Val Ser Met
            420                 425                 430
Trp Val Cys Arg Ala Leu Glu Glu Arg Ser Gln Gln Gly Pro Pro
        435                 440                 445
```

<210> SEQ ID NO 2
<211> LENGTH: 1772
<212> TYPE: DNA
<213> ORGANISM: Artificial Sequence
<220> FEATURE:
<223> OTHER INFORMATION: Description of Artificial Sequence: Synthetic Primer

<400> SEQUENCE: 2

```
atacattccc cttgtcactt cttggggctc ctaagtaggg gccagtcggt actccttgcc    60
gcaggatgtg agacccttta acctgtaatg ctgtggctgg cccttggccc ctttcgtgcc   120
atggagaacc aggtgctggt gattcggatc aagattccaa atagtggcgc ggtggactgg   180
accgtgcact ccgggccgca gttactcttc agggacgtgc tggatgtgat aggccaggtt   240
ctgcctgaag caacgacgac agcctttgaa tatgaagatg aagatggtga taggattaca   300
gtaagaagtg acgaagagat gaaggcaatg ctgtcctact attattccac agtaatggaa   360
cagcaagtaa atggccagct aatagagccg ctgcagatct ttccaagagc ctgcaagcct   420
cctggggaac ggaacataca tggcctgaag gtgaatacac gggctggacc atctcagcac   480
accagccctg tggtctcaga ttcacttcca gcaatagct tgaagaagtc ctcggctgaa   540
ctgagaaaga tactggccaa cggccagatg aatgaacaag acatacggta tcgagacacc   600
cttggtcatg gcaacggagg cacagtctac aaagcatatc atgtcccaag tgggaaaatc   660
ttagctgtaa aggttattct gttagacatc acactggagc ttcagaagca gatcatgtct   720
gagttggaaa ttctttataa gtgtgactca tcgtatatca taggatttta cggggcattt   780
tttgtagaaa acaggattttc gatttgtaca gaattcatgg atgggggtc tttggatgta   840
tataggaaaa ttccagagca cgtcctcgga agaattgcag tagcagttgt taaaggcctt   900
acctatctgt ggagtttaaa gattttacac agagatgtga agccttccaa catgcttgta   960
aacacaagcg gacaggtcaa gctgtgtgac ttcggcgtga gcacccagct ggtgaattct  1020
```

-continued

| | |
|---|---|
| atagccaaga cgtatgttgg aacaaatgct tatatggcac ccgaaaggat ttcaggagag | 1080 |
| cagtatggga tccattccga cgtgtggagc ttagggatct ctttcatgga gcttgctctt | 1140 |
| gggaggtttc catatcctca gattcagaaa aaccagggat ctttaatgcc tctccagctt | 1200 |
| ctgcagtgca ttgttgatga ggattcgccg gtccttccgc ttggagagtt ctcggagccg | 1260 |
| tttgtacatt tcatcactca gtgcatgagg aagcagccca aggaaagacc agcgcccgag | 1320 |
| gagctgatgg gtcacccatt catcgtgcag ttcaatgacg gaaacgccac tgtggtgtcc | 1380 |
| atgtgggttt gccgagctct ggaggagaga cggagccagc aggggccccc atgagacctc | 1440 |
| agcaggacac tgaccaccca ggaccaggca tcaaggtcac aacaagccgc gacccctctg | 1500 |
| tctgctgcct gattgggaag agatgtactg gcacagctc ctgctttcac cttctacctt | 1560 |
| acctgggagt cttcaagaag ggtggtctct gccgaacccc tcaccactgg tagggaggag | 1620 |
| gcactgacaa tggcaggtgg agatggtgca gggttgggt gatgaggtta tggaacctcc | 1680 |
| tctggcccca ccctcatctc tccctactgt tgtaaagggt cagcctatca gcagcactga | 1740 |
| tgggaataaa gtattactgc tttggattgt ag | 1772 |

<210> SEQ ID NO 3
<211> LENGTH: 1493
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 3

| | |
|---|---|
| cggacgtgct ggatgtgata ggccaggttc tgcctgaagc aacgacgaca gcctttgaat | 60 |
| tattattcca cagtaatgga acagcaagta aatggccagc taatagagcc gctgcagatc | 120 |
| tttccaagag cctgcaagcc tcctgggaa cggaacatac atggcctgaa ggtgaataca | 180 |
| cgggctggac catctcagca caccagcct gtggtctcag attcacttcc aagcaatagc | 240 |
| ttgaagaagt cctcggctga actgagaaag atactggcca acggccagat gaatgaacaa | 300 |
| gacatacggt atcgagacac ccttggtcat ggcaacggag gcacagtcta caaagcatat | 360 |
| catgtcccaa gtgggaaaat cttagctgta aaggttattc tgttagacat cacactggag | 420 |
| cttcagaagc agatcatgtc tgagttggaa attctttata agtgtgactc atcgtatatc | 480 |
| ataggatttt acgggcatt ttttgtagaa acaggatttt cgatttgtac agaattcatg | 540 |
| gatgggggt ctttggatgt atataggaaa attccagagc acgtcctcgg aagaattgca | 600 |
| gtagcagttg ttaaaggcct tacctatctg tggagtttaa agattttaca cagagatgtg | 660 |
| aagccttcca acatgcttgt aaacacaagc ggacaggtca agctgtgtga cttcggcgtg | 720 |
| agcacccagc tggtgaattc tatagccaag acgtatgttg aacaaatgc ttatatggca | 780 |
| cccgaaagga tttcaggaga gcagtatggg atccattccg acgtgtggag cttagggatc | 840 |
| tctttcatgg agcttgctct tgggaggttt ccatatcctc agattcagaa aaccaggga | 900 |
| tctttaatgc ctctccagct tctgcagtgc attgttgatg aggattcgcc ggtccttccg | 960 |
| cttggagagt tctcggagcc gtttgtacat ttcatcactc agtgcatgag gaagcagccc | 1020 |
| aaggaaagac cagcgcccga ggagctgatg ggtcacccat tcatcgtgca gttcaatgac | 1080 |
| ggaaacgcca ctgtggtgtc catgtgggtt tgccgagctc tggaggagag acggagccag | 1140 |
| caggggcccc catgagacct cagcaggaca ctgaccaccc aggaccaggc atcaaggtca | 1200 |
| caacaagccg cgacccctct gtctgctgcc tgattgggaa gagatgtact gggcacagct | 1260 |

-continued

```
cctgctttca ccttctacct tacctgggag tcttcaagaa gggtggtctc tgccgaaccc    1320
ctcaccactg gtagggagga ggcactgaca atggcaggtg agatggtgc agggttgggg    1380 tgatgaggtt atggaacctc ctctggcccc accctcatct ctccctactg ttgtaaaggg    1440
tcagcctatc agcagcactg atgggaataa agtattactg ctttggattg tag           1493
```

<210> SEQ ID NO 4
<211> LENGTH: 359
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 4

```
Met Glu Gln Gln Val Asn Gly Gln Leu Ile Glu Pro Leu Gln Ile Phe
  1               5                  10                  15

Pro Arg Ala Cys Lys Pro Pro Gly Glu Arg Asn Ile His Gly Leu Lys
             20                  25                  30

Val Asn Thr Arg Ala Gly Pro Ser Gln His Thr Ser Pro Val Val Ser
         35                  40                  45

Asp Ser Leu Pro Ser Asn Ser Leu Lys Lys Ser Ser Ala Glu Leu Arg
     50                  55                  60

Lys Ile Leu Ala Asn Gly Gln Met Asn Glu Gln Asp Ile Arg Tyr Arg
 65                  70                  75                  80

Asp Thr Leu Gly His Gly Asn Gly Gly Thr Val Tyr Lys Ala Tyr His
                 85                  90                  95

Val Pro Ser Gly Lys Ile Leu Ala Val Lys Val Ile Leu Leu Asp Ile
            100                 105                 110

Thr Leu Glu Leu Gln Lys Gln Ile Met Ser Glu Leu Glu Ile Leu Tyr
        115                 120                 125

Lys Cys Asp Ser Ser Tyr Ile Ile Gly Phe Tyr Gly Ala Phe Phe Val
    130                 135                 140

Glu Asn Arg Ile Ser Ile Cys Thr Glu Phe Met Asp Gly Gly Ser Leu
145                 150                 155                 160

Asp Val Tyr Arg Lys Ile Pro Glu His Val Leu Gly Arg Ile Ala Val
                165                 170                 175

Ala Val Val Lys Gly Leu Thr Tyr Leu Trp Ser Leu Lys Ile Leu His
            180                 185                 190

Arg Asp Val Lys Pro Ser Asn Met Leu Val Asn Thr Ser Gly Gln Val
        195                 200                 205

Lys Leu Cys Asp Phe Gly Val Ser Thr Gln Leu Val Asn Ser Ile Ala
    210                 215                 220

Lys Thr Tyr Val Gly Thr Asn Ala Tyr Met Ala Pro Glu Arg Ile Ser
225                 230                 235                 240

Gly Glu Gln Tyr Gly Ile His Ser Asp Val Trp Ser Leu Gly Ile Ser
                245                 250                 255

Phe Met Glu Leu Ala Leu Gly Arg Phe Pro Tyr Pro Gln Ile Gln Lys
            260                 265                 270

Asn Gln Gly Ser Leu Met Pro Leu Gln Leu Leu Gln Cys Ile Val Asp
        275                 280                 285

Glu Asp Ser Pro Val Leu Pro Leu Gly Glu Phe Ser Glu Pro Phe Val
    290                 295                 300

His Phe Ile Thr Gln Cys Met Arg Lys Gln Pro Lys Glu Arg Pro Ala
305                 310                 315                 320
```

-continued

```
Pro Glu Glu Leu Met Gly His Pro Phe Ile Val Gln Phe Asn Asp Gly
                325                 330                 335

Asn Ala Thr Val Val Ser Met Trp Val Cys Arg Ala Leu Glu Glu Arg
            340                 345                 350

Arg Ser Gln Gln Gly Pro Pro
        355
```

◄

TRANSGENIC MICE COMPRISING A CONSTITUTIVELY-ACTIVATED MEK5 AND EXHIBITING CARDIAC HYPERTROPHY AND DILATED CARDIOMYOPATHY

This application claims benefit of priority to U.S. Provisional Application Ser. No. 60/295,875, filed Jun. 4, 2001, the entire content of which is hereby incorporated by reference.

The government owns rights in the present invention pursuant to grant number HD-08363 from the National Institutes of Health.

BACKGROUND OF THE INVENTION

1. Field of the Invention

The present invention relates generally to the fields of developmental biology and molecular biology. More particularly, it concerns gene regulation and cellular physiology in cardiomyocytes.

2. Description of Related Art

Cardiac cells do not divide after birth, so both normal growth of the myocardium as well as stress-induced myocardial remodeling must take place through hypertrophic growth without cell division (MacLellan and Schneider, 2000). Cardiac hypertrophy can occur by an increase in width of myofibrils, resulting in a thickening of the myocardial wall or "concentric hypertrophy," or by an increase in myofibril length, producing chamber dilation or "eccentric hypertrophy." These contrasting forms of hypertrophy are coupled to parallel versus serial assembly of sarcomeres, respectively.

In the case of normal physiological growth or exercise-induced hypertrophy, concentric and eccentric hypertrophy occur simultaneously and in a balanced manner, enabling the heart to increase pumping capacity in response to increased demand. Disease states that put stress on the heart can also induce hypertrophy. Depending on the stimulus, however, either concentric or eccentric hypertrophy may predominate. Although hypertrophy may initially compensate for the additional demands placed on the heart by disease, almost inevitably continued stress results in decompensation and the development of hypertrophic or dilated cardiomyopathy. In order for any form of hypertrophic remodeling to occur, stress stimuli must activate signaling pathways that regulate protein synthesis, sarcomeric assembly and organization, and gene expression (Chien, 1999; Nicol et al., 2000; Sugden and Clerk, 1998).

Mitogen-activated protein kinase (MAPK) pathways provide an important connection between external stimuli that activate a wide variety of cell-signaling systems and the nucleus. At the core of each MAPK cascade is a three-kinase module in which the most downstream member, the MAPK, is activated by a MAPK kinase (MAPKK or MEK), which is in turn activated by a MAPKK kinase (MAPKKK or MEKK) (English et al., 1999a). MAPKs can be divided into three major subfamilies based on sequence homology: the extracellularly-responsive kinases (ERKs), the c-Jun $NH_2$-terminal kinases (JNKs), also known as stress-activated protein kinases (SAPKs), and the p38-MAPKs. In the heart, all three classes of MAP kinases are activated by G-protein coupled receptor (GPCR) agonists, stretch, and certain types of stress, including ischemia (Abe et al., 2000; Ruwhof and van der Laarse, 2000; Sugden and Clerk, 1998). A critical role for MAPK pathways in the development of hypertrophy in vivo has been demonstrated by the finding that transgenic expression of a MAP kinase phosphatase in the mouse heart can attenuate hypertrophy induced by aortic banding and catecholamine infusion (Bueno et al., 2001). The role of individual MAPK pathways in various aspects of the hypertrophic response is more controversial (Sugden and Clerk, 1998).

ERK5, also known as big MAPK 1 (BMK1), has an amino terminal domain that is homologous to ERKs 1 and 2, but has unique carboxyl-terminal and loop-12 domains (Lee et al., 1995; Zhou et al., 1995). MEK5, the activating MAPKK for ERK5, is a highly specific ERK5 kinase and does not activate other MAPKs even when overexpressed in cultured cells (English et al., 1995; Zhou et al., 1995). MEK5-ERK5 signaling has been shown to be activated by growth stimuli including serum and ligands for tyrosine kinase and GPCRs (Fukuhara et al., 2000; Kamakura et al., 1999; Kato et al., 1997), as well as by oxidative and osmotic stress (Abe et al., 1996). Signaling by this MAPK module has not been studied in detail in cardiac cells, but one report suggests that ERK5 may be regulated differently from ERK1/2 in these cells (Takeishi et al., 1999). Interestingly, the MEK1 inhibitors PD098059 and U0126 also inhibit activation of ERK5 (Kamakura et al., 1999), suggesting that functions previously attributed to ERK1/2 may also be mediated by ERK5.

SUMMARY OF THE INVENTION

Thus, in accordance with the present invention, there is provided a method for inhibiting cardiac hypertrophy in a subject comprising administering to said subject an amount of a composition effective to inhibit MEK5 activity, whereby inhibition of MEK5 activity inhibits cardiac hypertrophy. In another embodiment, there is provided a method for inhibiting dilated cardiomyopathy in a subject comprising administering to said subject an amount of a composition effective to inhibit MEK5 activity, whereby inhibition of MEK5 activity inhibits dilated cardiomyopathy. In yet another embodiment, there is provided a method for inhibiting heart failure in a subject comprising administering to said subject an amount of a composition effective to inhibit MEK5 activity, whereby inhibition of MEK5 activity inhibits heart failure.

The method may further comprise administering to said subject a second anti-hypertrophic composition, for example, "beta blockers," anti-hypertensives, cardiotonics, anti-thrombotics, vasodilators, hormone antagonists, endothelin antagonists, calcium channel blockers, phosphodiesterase inhibitors, angiotensin type 2 antagonists or cytokine blockers/inhibitors. The composition may be a MEK5 antisense molecule, an anti-MEK5 antibody, or a MEK5 ribozyme. The composition may inhibit or block MEK5 function, inhibit or block MEK5 transcription, inhibit or block MEK5 translation, inhibit or block MEK5 processing, or decrease MEK5 half-life.

Alternatively, the composition may be a nucleic acid encoding a dominant negative MEK5 polypeptide, for example, a dominant-negative MEK5 polypeptide that contains at least one mutation in the ATP binding site, under the control of a promoter active in cardiac cells of said subject. The promoter may be myosin light chain-2 promoter, the α actin promoter, the troponin 1 promoter, the $Na^+/Ca^{2+}$ exchanger promoter, the dystrophin promoter, the creatine kinase promoter, the alpha7 integrin promoter, the brain natriuretic peptide promoter, the α B-crystallin/small heat shock protein promoter, α myosin heavy chain promoter or the ANF promoter. The nucleic acid may further comprise a polyadenylation signal, and may be comprised within an expression vector, which can include an origin of replication and a selectable marker gene. Expression vectors include both plasmids and viral vectors, for example, adenovirus, retrovirus, adeno-associated virus, vaccinia virus, herpesvirus or polyoma virus. Vectors may be comprised with a liposome. The viral vector may be comprised within a viral particle. The viral vector may be replication defective.

In yet another embodiment, there is provided a method of inhibiting cardiac myocyte elongation in a cell comprising administering to said cell an amount of a composition effective to inhibit MEK5 activity, whereby inhibition of MEK5 activity inhibits cardiac myocyte elongation. In still yet another embodiment, there is provided a method of restoring balance between serial and parallel sarcomere assembly in a cell comprising administering to cell an amount of a composition effective to inhibit MEK5 activity, whereby inhibition of MEK5 activity restores the balance between serial and parallel sarcomere assembly. In yet a further embodiment, there is provided a method of inhibiting ventricular wall thinning in a subject comprising administering to said subject an amount of a composition effective to inhibit MEK5 activity, whereby inhibition of MEK5 activity inhibits ventricular wall thinning. In still yet a further embodiment, there is provided a method of reducing sensitivity of MEK5 to G-protein coupled receptor ("GPCR") agonists in a cell comprising administering to said cell an amount of a composition effective to inhibit MEK5 activity, whereby inhibition of MEK5 activity reduces sensitivity of MEK5 to GPCR agonists. In yet even a further embodiment, there is provided a method for inhibiting MEK5-induced hypertrophic signaling in a cell comprising administering to said cell an amount of a composition effective to inhibit MEK5 activity, whereby inhibition of MEK5 activity inhibits MEK5-induced cardiac hypertrophic signalling.

In an additional embodiment, there is provided a non-human transgenic mammal, cells of which comprise a constitutively-activated MEK5 coding region under the control of a heterologous promoter, wherein said constitutively activated MEK5 is expressed in said cells. The promoter may be an inducible promoter, a tissue specific promoter, or a constitutive promoter. The activated MEK5 may contain phosorylation sites substituted with acidic residues. In a similar embodiment, there is provided a MEK5 coding region under the control of a promoter, wherein said MEK5 is expressed in said cells. In yet another related embodiment, there is provide a non-human transgenic mammal, cells of which comprise a dominant-negative MEK5 coding region under the control of a promoter, wherein said dominant-negative MEK5 is expressed in said cells. The dominant-negative MEK5 coding region may contain at least one mutation in the ATP binding site.

In a further embodiment, there is provided a method of screening for an inhibitor of cardiac hypertrophy comprising (a) providing a cell comprising a MEK5 coding region under the control of a promoter, wherein MEK5 is expressed therefrom; (b) contacting said cell with a candidate inhibitor substance; and (c) determining MEK5 activity of said cell; wherein a reduction in MEK5 activity in the presence of said candidate inhibitor substance, as compared to the MEK5 activity in the absence of said candidate inhibitor substance, indicates that said candidate inhibitor substance is an inhibitor of MEK5 activity, and hence, an inhibitor of cardiac hypertrophy. The promoter may be heterologous to said MEK5 coding region. The transgenic cell may be cardiomyocyte located in a non-human transgenic animal. The assay may further comprise determining the activity of MEK5 in a comparable cell in the absence of said candidate inhibitor substance. The candidate inhibitor substance may be a nucleic acid or a small molecule. The step of determining may comprise measuring MEK5 kinase activity, measuring MEK5-induced cardiac hypertrophy signaling, measuring one or more aspects of cellular morphology (e.g., cell elongation, cell size and cell contractility) or measuring cardiac hypertrophy, or a symptom thereof (e.g., hypertrophic or fetal gene expression (ANF, alpha skeletal actin, myosin heavy chain gene switch or BNF), fibrosis, reduced cardiac contractility (measured by LV dp/dt, LV ejection fraction, RV ejection fraction, or altered LV pressure/volume loops), or increased heart/body, heart/brain weight or heart/tibia weight ratios). The MEK5 coding region may encode a constitutively-activated MEK5, for example, an activated MEK5 containing phosorylation sites substituted with acidic residues. The method may further comprise contacting said cell is a G-protein coupled receptor (GPCR) agonist, for example, an IL-6 family cytokine, leukemia inhibitory factor, or cardiotrophin-1.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Lysates were prepared 48 hrs post-infection and 5 $\mu$g of protein was separated by SDS-PAGE and immunoblotted with anti-HA antibody. (FIG. 2B) Immunoprecipitations were performed on 100 $\mu$g of protein with anti-HA antibody. Kinase assays were performed with immunoprecipitated HA-MEK5 using GST-ERK5KM$\Delta$ substrate in the presence of [$\gamma$-$^{32}$P]-ATP. GST-ERK5KM$\Delta$ phosphorylation was detected after SDS-PAGE by autoradiography. Serum-deprived cardiomyocytes were infected at an moi of 100 with adenovirus expressing (FIG. 2C) $\beta$-galactosidase, (FIG. 2D) MEK1CA and (FIG. 2E and FIG. 2G) MEK5DD or not infected and treated with (FIG. 2F and FIG. 2H) PE (50 $\mu$M). Cells were fixed 72 hours post-infection and immunostained with anti-sarcomeric $\alpha$-actinin antibody. Note that cells in FIGS. 2G and H are shown at higher magnification than cells in FIGS. 2C–F. Bar=20 $\mu$m.

(FIG. 3A) uninfected cells treated with LIF (FIG. 3B) AdMEK5KM-infected cells treated with LIF (FIG. 3C) Adβ-gal-infected cells treated with LIF (FIG. 3D) uninfected cells treated with PE (FIG. 3E) AdMEK5KM-infected cells treated with PE (FIG. 3F) Adβ-gal-infected cells treated with PE. Bar=20 μm.

(FIG. 4A) Cardiomyocytes were either not infected (−) or infected with MEK5WT, MEK5KM or β-gal adenoviruses at an moi of 20 and serum-deprived. Thirty-six hours post-infection, cells were either not treated or treated with 50 μM PE (black bar) or 1000 units/ml LIF (white bar) for an additional 24 hours. RNA was prepared and used for dot blots with oligonucleotide probes specific for skeletal α-actin, ANF or BNP. Signal intensity was quantitated using a Phosphor Imager. The average fold induction±SD of three independent experiments is shown. "-fold" induction is relative to uninfected cells without PE or LIF treatment. (FIG. 4B) Cardiomyocytes were either not infected or infected with MEK5DD or β-gal adenoviruses at an moi of 20 and serum-deprived. Forty-eight hours post-infection, the cells were harvested and RNA was prepared. Transcript levels for α-skeletal actin, ANF or BNP were determined as described in FIG. 4A. "-fold" induction is relative to uninfected cells.

(FIG. 5A) Expression of HA-tagged MEK5DD was analyzed in different lines of transgenic mice by immunoblotting with anti-HA antibody. Lines of MEK5DD-transgenic mice are indicated by identifying numbers. For each line, lysate was prepared from two hearts and loaded in adjacent lanes. Expression of (FIG. 5B) MEK5 and (FIG. 5C) ERK5 was analyzed in wild-type and line 367 MEK5DD-transgenic mice by immunoblotting with L610 rabbit anti-MEK5 antiserum and rabbit anti-ERK5. Bands which are either nonspecific (asterisk) or degradation products (arrowhead) are indicated. Note reduced mobility of ERK5 in transgenic animals relative to wild-type.

(FIG. 7A) Hearts were removed from wild-type and MEK5DD-transgenic mice at 3 weeks, 6 weeks, and 12 weeks of age. Hearts were fixed in 10% PBS-buffered formalin and photographed. (FIG. 7B) Hearts from 12 week-old MEK5DD-transgenic and wild-type mice were fixed and sectioned longitudinally or at the midsagittal level parallel to the base and stained with hematoxylin-eosin. ra, right atrium; la, left atrium; rv, right ventricle; lv, left ventricle.

DESCRIPTION OF ILLUSTRATIVE EMBODIMENTS

Figure 1:
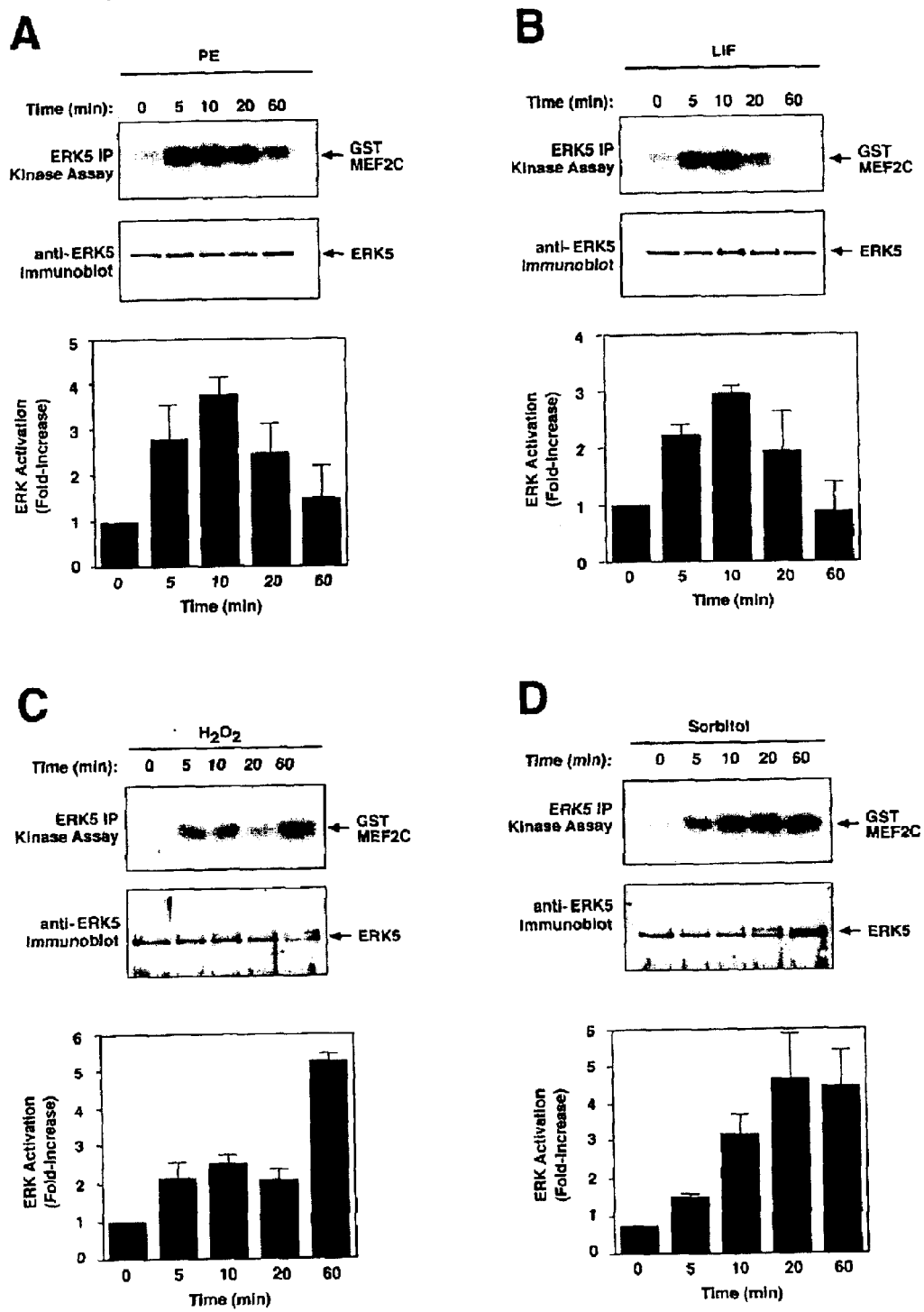
FIGS. 1A–D. Activation of endogenous ERK5 by hypertrophic and stress agents. Serum-deprived neonatal rat cardiomyoctyes were treated with (FIG. 1A) 100 $\mu$M PE, (FIG. 1B) 1000 units/ml LIF, (FIG. 1C) 200 $\mu$M $H_2O_2$, and (FIG. 1D) 0.3M sorbitol for the indicated times, harvested, and ERK5 kinase activity was measured. Top, ERK5 was immunoprecipitated from 200 $\mu$g of cellular lysate with an antibody specific for the carboxyl-terminal 20 amino acids. Kinase assays were performed with immunoprecipitated ERK5 using GST-MEF2C substrate in the presence of [$\gamma$-$^{32}$P]-ATP. GST-MEF2C phosphorylation was detected by autoradiography after SDS-PAGE. Middle, immunoblotting was performed on immunoprecipitated material using rabbit anti-ERK5 antibody. Bottom, levels of $^{32}$P-phosphorylated GST-MEF2C were quantitated with a Phosphor Imager. The averaged result±standard deviation (SD) of three independent experiments is shown.

The inventors investigated the role of the MEK5-ERK5 signaling module in hypertrophic signaling in cardiac myocytes in vitro and in vivo. The results presented in the examples below demonstrate that ERK5 is activated by PE and LIF, as well as the stress stimuli, $H_2O_2$ and sorbitol. Adenoviral-mediated expression of constitutively activated MEK5 induced cardiomyocytes to assume a highly elongated morphology, reminiscent of the phenotype induced by LIF and the related cytokine, CT-1. Consistent with the potential involvement of MEK5 in the LIF signaling pathway, a dominant negative MEK5 mutant blocked LIF-induced elongation of cardiomyocytes. In contrast, dominant negative MEK5 had no effect on LIF-induced assembly of sarcomeres, and actually increased cell area relative to LIF treatment alone. The outcome of MEK5 activation in vitro is highly unique—no other signaling molecule has been shown to be sufficient to induce the elongated phenotype typical of CT-1/LIF-activated signaling in cardiomyocytes. These effects may reflect a similar function in vivo because transgenic mice that overexpress activated MEK5 under control of the α-MHC promoter develop severe dilated cardiomyopathy characterized by thinning of the ventricular walls and decreased cross-sectional area of individual myocytes.

Thus, in accordance with the present invention, the inventors propose that MEK5 is a suitable point for intervening in molecular events that lead to or contribute to cardiac hypertrophy and/or dilated cardiomyopathy. In particular, inhibition of MEK5 activity will lead to decrease signalling of the pathways and reduce or eliminate the effects on sarcomere assembly. Also provided are transgenic animals and methods of screening for inhibitors of MEK5.

I. Cytokine Involvement in Cardiac Gene Expression and Signalling

LIF and CT-1 belong to the IL-6 family of cytokines and bind to a heterodimer of gp130 and the LIF receptor (Wollert and Chien, 1997). A plethora of hormones and peptide growth factors can stimulate a hypertrophic phenotype in cultured cardiomyocytes. However, LIF and CT-1 are unique in their ability to induce primarily serial assembly of sarcomeres and an elongated morphology (Wollert et al., 1996). The mechanism by which LIF and CT-1 induce serial assembly of sarcomeres is not known. Several signaling pathways have been implicated in the induction of the hypertrophic phenotype by LIF and CT-1 (Kato et al., 2000; Kunisada et al., 1996; Oh et al., 1998). However, with the exception of the original characterization of CT-1-induced hypertrophy (Wollert et al., 1996), all of these studies have defined morphological hypertrophy as an overall increase in cell area without describing contributions of length and width. One study implicated Janus kinase (JAK)/signal transducer and activator of transcription (STAT) but not ERK1/2 or phosphatidylinositide 3-kinase (PI3-K) in CT-1-induced organization of sarcomeres (Kodama et al., 2000), but the distinction between serial versus parallel assembly of sarcomeres was not addressed.

Figure 10:
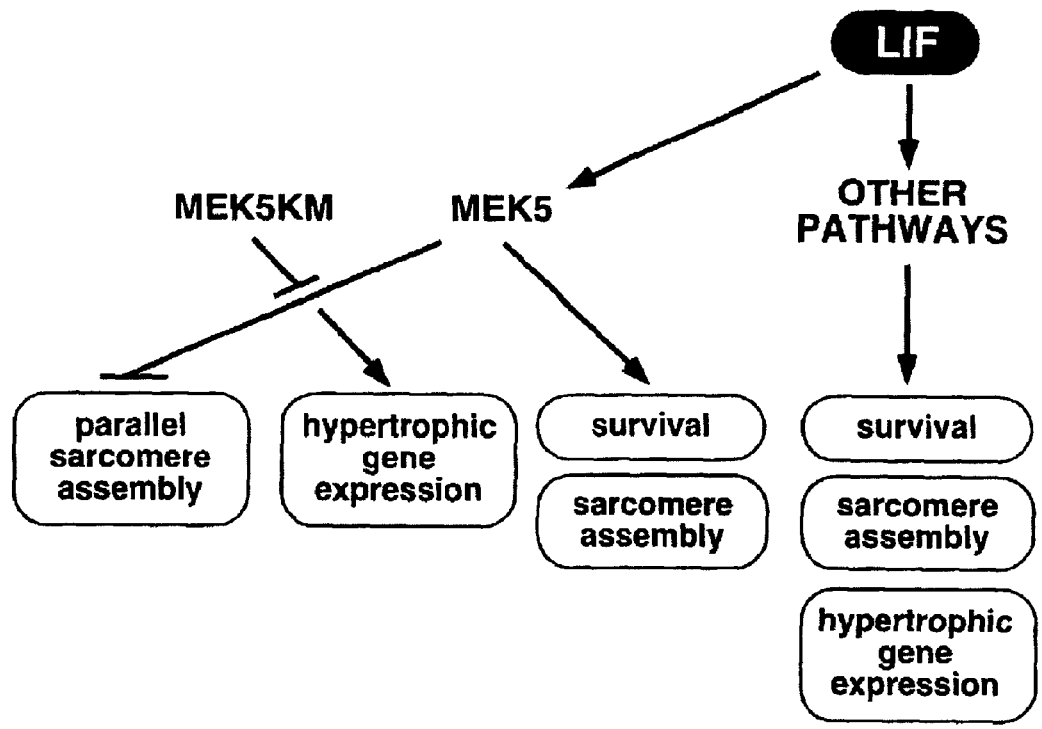
FIG. 10. MEK5 induces cardiomyocyte elongation by interfering with parallel assembly of sarcomeres. Model for LIF-induced cardiomyocyte elongation mediated by MEK5 inhibition of parallel assembly of sarcomeres. Other signaling molecules implicated downstream of LIF include MEK1, JAK/STAT, PI3-K, CaMK, and calcineurin.

Hypertrophy induced by GPCR agonists, as well as normal physiological growth in vivo, involves a balance between parallel and serial assembly of sarcomeres. In the case of LIF treatment or overexpression of activated MEK5, the balance is shifted so that serial assembly of sarcomeres predominates. In spite of the fact that AdMEK5DD-infected cells appear highly elongated, morphological measurement shows that AdMEK5DD- and AdMEK1CA-infected cells are comparable in length (Table 1), and that the length-to-width ratio is dramatically altered in AdMEK5DD-infected cells. This implies that although serial assembly of sarcomeres occurs normally in these cells, parallel assembly is almost entirely absent. This distinction is further illustrated by results with AdMEK5KM. LIF-treated cells infected with the dominant negative MEK5 adenovirus are similar to PE-treated or AdMEK1CA-infected cardiomyocytes in appearance, suggesting that a balance between parallel and serial assembly of sarcomeres has been restored. This result can be explained by a model in which LIF and MEK5DD induce myofibril formation and at the same time specifically interfere with assembly of sarcomeres in parallel (FIG. 10). Relief of this interference by dominant negative MEK5 would then allow parallel assembly of sarcomeres in response to LIF. Results with activated and dominant negative MEK5 further imply that although activated MEK5 is sufficient to induce a specific pattern of sarcomere assembly, MEK5 signaling is not essential for sarcomere formation per se. The ability of LIF and MEK5 to differentially regulate parallel and serial assembly of sarcomeres implies that there is something inherently different about these two processes. Further investigation into the mechanism by which MEK5 directs sarcomere assembly should provide novel insight into regulation of myofibril formation.

Treatment of cardiomyocytes with LIF and CT-1 induces expression of fetal and immediate early genes (Wollert et al., 1996). Inhibitor studies have shown that activation of ERK1/2, $Ca^{2+}$/calmodulin-dependent protein kinase (CaMK)II and IV, and calcineurin signaling all contribute to full induction of ANF, BNP, and α-skeletal actin by IL-6 family cytokines (Kato et al., 2000; Kodama et al., 2000; Wollert et al., 1996). Additional signaling pathways may play more limited roles (Kodama et al., 2000). Our results demonstrate that dominant negative MEK5 partially blocks and wild-type MEK5 increases induction of ANF, BNP, and α-skeletal actin by PE and LIF. Activated MEK5 also strongly induced α-skeletal actin, but only weakly induced ANF and BNP. Therefore, it is likely that MEK5 synergizes with MEK1/2 or calcium-regulated signaling pathways to fully induce the fetal gene expression program.

It seems paradoxical that ERK5 kinase activity is increased in response to stimuli that have dramatically different effects on cardiomyocyte phenotype. For example, LIF, PE and stress agents all activate ERK5, but in each case the outcome is different: LIF induces cellular elongation; PE induces overall hypertrophy; and $H_2O_2$ and sorbitol induce rapid apoptosis. Combinatorial activation of signaling pathways may be a key factor in determining the outcome of MAPK activation in cardiomyocytes. Expression of activated MKK6, a p38-specific MAPKK, in cardiomyocytes is sufficient to induce all the characteristic features of hypertrophy, whereas activated MKK3, another p38-specific MAPKK, can induce either hypertrophy or apoptosis, depending on which isoform of p38 is coexpressed (Wang et al., 1998a; Wang et al., 1998b). The level and temporal pattern of activation may also be key factors in determining cardiomyocyte response. For example, low levels of Gαq signaling have been associated with hypertrophy, whereas, higher levels can induce apoptosis (Adams et al., 1998). ERK1/2-signaling has been shown to protect cardiomyocytes from stress-induced apoptosis and ERK5 may have a similar function (Bueno et al., 2000). It also is important to note that increased catalytic activity of ERK5 may not be the only relevant outcome of MEK5 signaling. MEK5 may have other uncharacterized targets and ERK5 may have functions that are independent of kinase activity. Of note, a recent study showed that ERK5 activation of the MEF2 transcription factor did not require the catalytic domain of the kinase (Kasler et al., 2000).

In many cases of concentric hypertrophy, a transition to dilated cardiomyopathy occurs during the end stages of heart failure. Although there is evidence to suggest that apoptosis of cardiomyocytes may be responsible for this transition (MacLellan and Schneider, 1997), Gerdes and coworkers have found that myocyte lengthening alone can account for chamber dilation in the progression to heart failure of the spontaneously hypertensive rat (Tamura et al., 1998). The inventors examined dilated MEK5DD-transgenic hearts, but found no evidence for increased levels of apoptosis or necrosis.

A large number of mouse models of heart failure have been described, many of them produced by overexpression of constitutively active signaling molecules (Ikeda et al., 2000). The inventors have been particularly interested in the role that calcium-dependent signaling pathways play in the development of hypertrophic cardiomyopathy (Frey et al., 2000). The inventors have previously shown that cardiac-specific expression of constitutively active forms of two calcium-dependent signaling molecules, calcineurin and CaMKIV, is sufficient to induce compensated concentric hypertrophy in mice (Molkentin et al., 1998; Passier et al., 2000). In both cases, the concentric hypertrophy eventually decompensates and the hearts undergo some degree of dilation. The inventors have not yet determined if MEK5/ERK5 signaling operates downstream of calcium-dependent signaling in these models, although ERK5 activation by $H_2O_2$ has previously been shown to be calcium-dependent (Abe et al., 1996).

Although experiments in cultured cardiomyocytes have provided substantial evidence supporting a role for each of the three major MAPK pathways in hypertrophy (Sugden and Clerk, 1998), until recently, the sufficiency of these molecules to induce a hypertrophic phenotype in vivo had not been examined. Surprisingly, despite similar effects in vitro, overexpression of these signaling molecules in vivo in the mouse heart produces very distinct phenotypes. While expression of constitutively active MEK1 in the mouse heart was sufficient to drive a compensated concentric hypertrophy, expression of transforming-growth-factor-β-activated kinase (TAK1), a MAPKKK for the p38 pathway, produced cardiac hypertrophy with interstitial fibrosis, apoptosis, and severe myocardial dysfunction (Bueno et al., 2000; Zhang et al., 2000). MEK5 and ERK5 are most closely related to components of the ERK1/2 signaling cascade, but appear to have distinct functions in regulating sarcomere assembly in cultured cardiomyocytes. Activation of MEK5 in the mouse heart produces a decompensated eccentric hypertrophy: a phenotype in stark contrast to the compensated concentric hypertrophy observed in MEK1-transgenic mice.

There is a tendency to generally catagorize different mouse models of cardiomyopathy as "dilated" or "hypertrophic" without more detailed consideration of the phenotypes. However, closer examination reveals that even among mouse models of dilated cardiomyopathy, disease phenotypes vary drastically. Hearts from desmin-null mice have been shown to progress through a concentric hypertrophy phase prior to dilation, and dilated hearts from mice overexpressing a dominant negative mutant of the transcription factor CREB exhibit a mixture of hypertrophied and atrophied cardiomyocytes (Fentzke et al., 1998; Milner et al., 1999). In contrast, transgenic expression of activated MEK5 produces a homogenous decrease in myocyte diameter without significant increases in apoptosis, necrosis, or fibrosis. In vivo, it is unlikely that a signaling pathway will be activated in isolation, so that the effects of MEK5 signaling may depend on the simultaneous activation of other signaling pathways, including other MAPK signaling pathways, $Ca^{2+}$-regulated signaling molecules, and rho-family small GTP-binding proteins. However, the unique nature of the MEK5DD-induced phenotype in vitro and in vivo suggests that further examination of the mechanism of MEK5-induced eccentric hypertrophy may provide novel insight into the fundamental mechanisms underlying regulation of sarcomere assembly and the role that this process plays in development of dilated cardiomyopathy.

II. Nucleic Acids

Thus, in one aspect, the present invention provides nucleic acid sequences encoding MEK5. The present invention is not limited in scope to any specific nucleic acid sequences disclosed herein as one of ordinary skill in the art could, using these nucleic acid sequences, readily identify related homologs, including, for example, homologs present in any of various species (e.g., rat, rabbit, dog, monkey, gibbon, chimp, ape, baboon, cow, pig, horse, sheep, cat and other species).

As discussed below, a "MEK5 nucleic acid sequence" may contain a variety of different bases and yet still produce a MEK5 polypeptide according to the present invention. Such polypeptides will generally be functionally equivalent to, and/or structurally indistinguishable, from the human, mouse and other genes disclosed herein. Additionally, nucleic acid sequences encoding fragments of MEK5 are provided herein. For example, fragments having increased activity as compared with the full-length MEK5 polypeptide are described. Similarly, it will be readily recognized that fragments may be employed as probes, for example in the isolation of homologous sequences. Thus, as will be apparent to those of skill in the art, fragments of the MEK5-encoding nucleic acid sequences as well as homologs thereof are likewise contemplated herein.

Similarly, any reference to a nucleic acid should be read as encompassing vectors and host cells containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of MEK5.

A. Nucleic Acids Encoding MEK5

Nucleic acids according to the present invention may encode an entire MEK5 gene, a domain of MEK5, or any other fragment of MEK5 as set forth herein. The nucleic acid may be derived from genomic DNA, i.e., cloned directly from the genome of a particular organism. In preferred embodiments, however, the nucleic acid comprises complementary DNA (cDNA). Also contemplated is a cDNA plus a natural intron or an intron derived from another gene; such engineered molecules are sometime referred to as "minigenes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given MEK5 polynucleotide may be represented by natural or synthetic variants that have slightly different nucleic acid sequences but, nonetheless, encode the same or homologous protein (see Table 1 below).

As used in this application, the term "a polynucleotide encoding a polypeptide" refers to a nucleic acid molecule that has been isolated free of total cellular nucleic acid. In exemplary embodiments, the invention concerns a nucleic acid sequence essentially as set forth in SEQ ID NO: 1. The term "comprises SEQ ID NO: 1" means that the nucleic acid sequence substantially corresponds to a portion of SEQ ID NO:1. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |

TABLE 1-continued

| Amino Acids | | | Codons |
|---|---|---|---|
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 are contemplated. Sequences that are essentially the same as those set forth in SEQ ID NO:1 also may be functionally defined as sequences that are capable of hybridizing to a nucleic acid segment containing the complement of SEQ ID NO:1 under standard conditions.

The DNA segments of the present invention include those encoding biologically functional equivalent MEK5 proteins, peptides and fragments thereof, as described elsewhere herein. Such sequences may arise as a consequence of codon redundancy and/or amino acid functional equivalency that are known to those of skill in the art. For example, polynucleotides encoding MEK5 polypeptides analogous to the exemplary MEK5 protein of SEQ ID NO:2 are likewise contemplated herein. As discussed further below, and as known to those of skill in the art, various amino acid substitutions, deletions and/or additions may be made to a known amino acid sequence without adversely affecting the function and/or usefulness thereof. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequences set forth herein, for example in SEQ ID NO:1. Nucleic acid sequences that are "complementary" are those that are capable of base-pairing according to the standard Watson-Crick complementary rules. As used herein, the terms "complementary sequences" and "essentially complementary sequences" means nucleic acid sequences that are substantially complementary to, as may be assessed by the same nucleotide comparison set forth above, or are able to hybridize to a nucleic acid segment of one or more sequences set forth herein, for example SEQ ID NO:1, under relatively stringent conditions such as those described herein. Such sequences may encode an entire MEK5 protein or peptide or functional or non-functional fragments thereof.

The hybridizing segments may be short oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 750, 1000, 1250, 1500, 2000, 2500, 3000 or 4000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mm KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

One method of using probes and primers of the present invention is in the search for genes related to MEK5 proteins and peptides, including for example, MEK5 proteins from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred.

The technique typically employs a bacteriophage vector that exists in both a single stranded and double-stranded form. Typical vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject. Thus, antisense molecules are one potential class of MEK5 inhibitor.

Antisense constructs may be designed to bind to the promoter and/or other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen postions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction. Thus, ribozymes are another potential class of MEK5 inhibitor.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express a MEK5 mRNA or polypeptide product. Expression requires that appropriate signals be provided in the vectors, including, for example, various regulatory elements, such as enhancers/promoters from viral and/or mammalian sources that are involved in driving expression of the genes of interest in host cells. Elements designed to optimize messenger RNA stability and translatability in host cells also can be used. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" or "expression cassette" is meant to include any type of genetic construct containing a nucleic acid coding for a gene product in which part or all of the nucleic acid encoding sequence is capable of being transcribed. The transcript may be translated into a protein or polypeptide, but it need not be. In certain embodiments, expression includes both transcription of a gene and translation of mRNA into a gene product. In other embodiments, expression only includes transcription of the nucleic acid encoding a gene of interest.

As used herein, regulatory elements (or sequences) are nucleotide sequences that enhance or otherwise modulate transcription and/or translation or that stabilize transcription and/or translation products. Thus, for example, promoters operably linked to a coding sequence of an expression construct enhance transcription of that coding sequence and polyadenylation sequences operably linked to a coding sequence modulate polyadenylation of the gene transcript. Exemplary regulatory sequences can include, without limitation, promoters, enhancers, introns, termination sequences, polyadenylation sequences, stabilization sequences and the like.

In certain embodiments, the nucleic acid encoding a gene product is operably linked and under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are typically composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, the human cytomegalovirus (CMV) immediate early gene promoter, the SV40 early promoter, the Rous sarcoma virus (RSV) long terminal repeat, a human elongation factor (hEF) promoter, rat insulin promoter or glyceraldehyde-3-phosphate dehydrogenase promoter can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. By way of illustration, a ubiquitous, strong (i.e., high activity) promoter may be employed to provide abundant gene expression in a group of host cells, or a tissue-specific promoter may be employed to target gene expression to one or more specific cell types. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole is typically able to stimulate transcription at a distance; this need not be true of a promoter region or its component elements. On the other hand, a promoter typically has one or more elements that direct initiation of RNA synthesis at a particular site and in a particular orientation, whereas enhancers generally lack these specificities. Promoters and enhancers are often overlapping and contiguous, often seeming to have a very similar modular organization.

Tables 2 and 3, provided below, list several regulatory elements that may be employed, in the context of the present invention, to regulate the expression of the gene of interest. This list is not intended to be exhaustive of all the possible elements involved in the promotion of gene expression but, merely, to be exemplary thereof. Other promoter/enhancer combinations (see, e.g., the Eukaryotic Promoter Data Base EPDB) could also be used to drive expression of the gene.

Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Human Elongation Factor-1A (hEF-1A or hEF-1α) | Uetsuki, et al., 1989; Wakabayashi-Ito, et al., 1994 |
| Prealbumin (Transthyretin) | Costa et al., 1988 |
| Elastase I | Omnitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |

TABLE 2-continued

Promoter and/or Enhancer

| Promoter/Enhancer | References |
|---|---|
| Hepatitis B Virus | Bulla et al., 1986; Jameel et al., 1986; Shaul et al., 1987; Spandau et al., 1988; Vannice et al., 1988 |
| Human Immuno-deficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Rous sarcoma virus (RSV) | Gorman, et al., 1982; Guzman, et al., 1993 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | ElA | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | ElA, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

In one aspect, tissue-specific promoters, e.g., cardiac-specific and/or fibroblast-specific promoters, are of particular interest. By way of illustration, cardiac-specific promoters include the myosin light chain-2 promoter (Franz et al., 1994; Kelly et al., 1995), the α actin promoter (Moss et al., 1996), the troponin 1 promoter (Bhavsar et al., 1996), the $Na^+/Ca^{2+}$ exchanger promoter (Barnes et al., 1997), the dystrophin promoter (Kimura et al., 1997), the creatine kinase promoter (Ritchie, 1996), the alpha7 integrin promoter (Ziober and Kramer, 1996), the brain natriuretic peptide promoter (LaPointe et al., 1996), the α B-crystallin/small heat shock protein promoter (Gopal-Srivastava, R., 1995), α myosin heavy chain promoter (Yamauchi-Takihara et al., 1989) and the ANF promoter (LaPoint et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, in which cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome entry site (IRES) elements are used to create multigene, or polycistronic, messages. IRES elements is believed to allow bypassing of the ribosome scanning model of 5' methylated Cap dependent translation and facilitate translation at internal sites (Pelletier and Sonenberg, 1988). By way of illustration, IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Polyadenylation Signals

In expression, one will typically include a polyadenylation signal to effect proper polyadenylation of the transcript. The nature of the polyadenylation signal is not believed to be crucial to the successful practice of the invention, and any of a number of such sequences may be employed. Exemplary embodiments include the SV40 polyadenylation signal, the bovine growth hormone polyadenylation signal and others which are convenient and/or known to function well in various target cells. Also contemplated as an element of the expression cassette is a transcriptional termination site. These elements can serve to enhance message levels and/or to minimize read through from the cassette into other sequences.

(v) Vectors

The term "vector" is used to refer to carrier molecules with which a nucleic acid sequence can be associated for introduction into a cell. The nucleic acid sequence can be "exogenous," (e.g., foreign to the cell into which it is introduced) or "endogenous" (e.g., the same as a sequence in the cell into which it is introduced. Exemplary vectors include plasmids, cosmids, viruses (bacteriophage, animal viruses, and plant viruses), and artificial chromosomes (e.g., YACs), lipid-based vectors (e.g., liposomes) and other macromolecular complexes capable of mediating delivery of a polynucleotide to a host cell. One of skill in the art would be well equipped to construct a vector through standard techniques, for example standard recombinant techniques such as described in Sambrook et al., 1989 and Ausubel et al., 1994, both incorporated herein by reference.

A large number of viral and non-viral vectors (including lipid-based and other synthetic delivery systems known in the art) can likewise be employed to deliver polynucleotides of the present invention. Such vectors may be modified, as known to those of skill in the art, to confer or enhance cell specificity. By way of illustration, the surface of viral vectors may be modified such that they preferentially or exclusively bind to and/or infect a particular target cell population.

As used herein, the term "expression vector" refers to a vector containing a nucleic acid sequence coding for at least part of a gene product capable of being transcribed. In some cases, the transcription product(s) are then translated into a protein, polypeptide, or peptide. In other cases, these sequences are not translated, for example, in the production of antisense molecules or ribozymes. Expression vectors can contain a variety of "control sequences," which refer to nucleic acid sequences that regulate the transcription and possibly translation of an operably linked coding sequence in a particular host organism. In addition to control sequences that govern transcription and translation, vectors and expression vectors may contain nucleic acid sequences that serve other functions as well for example as described infra.

(vi) Host Cells

As used herein, the terms "cell," "cell line," and "cell culture" may be used interchangeably. These terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand conditions under which to incubate such host cells to maintain them and to permit replication of a vector. Also understood and known are techniques and conditions that would allow large-scale production of vectors, as well as production of the nucleic acids encoded by vectors and their cognate polypeptides, proteins, or peptides.

(vii) Expression Systems

Numerous expression systems exist that comprise at least a part or all of the compositions discussed above.

Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ baculovirus expression system from CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

(viii) Gene Delivery Means

There are a number of ways in which a gene of interest, for example within an expression vector, may be introduced into cells. In certain embodiments of the invention, the gene delivery means comprises a virus or engineered construct derived from a viral genome. The ability of certain viruses to enter cells for example via receptor-mediated endocytosis and to express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). Although these viral vectors generally have a relatively fixed capacity for foreign DNA can accommodate up to 5–10 kb of foreign DNA and many different viral vectors can be readily introduced into a variety of different cells and animals (see, e.g., Nicolas and Rubenstein, 1988; Temin, 1986). Where viral vectors are employed to deliver the gene or genes of interest, it is generally preferred that they be replication-defective.

One of the preferred methods for in vivo gene delivery involves the use of an adenovirus expression vector. "Adenovirus expression vector" is meant to include those constructs containing adenovirus sequences sufficient to (a) support packaging of the construct and (b) to express polynucleotide that has been cloned therein. In this context, expression does not require that the gene product be synthesized.

An adenivorus expression vector comprises a genetically engineered form of adenovirus. Knowledge of the genetic organization of adenovirus, a linear, double-stranded DNA virus, allows substitution of large pieces of adenoviral DNA with foreign sequences (typically up to about 7 kB (Grunhaus and Horwitz, 1992)). Modified adenoviral and other viral vectors have also been constructed to provide for increased packaging capacity and are likewise contemplated herein. In contrast to retrovirus, the adenoviral infection of host cells does not generally result in chromosomal integration. Also, adenoviruses are structurally stable, and no genome rearrangement has been detected after extensive amplification. Adenovirus can infect various lineages of cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. In the case of adenovirus serotype 5 (Ad5), for example, both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is important to minimize this possibility by reducing or eliminating adnoviral sequence overlaps within the system and/or to isolate a single clone of virus from an individual plaque and examine its genomic structure.

Generation and propagation of replication-deficient adenovirus vectors depend on a unique helper cell line, such as the human 293 cell line, which was transformed from human embryonic kidney cells by Adenovirus type 5 DNA fragments to constitutively expresses E1 proteins (Graham et al., 1977). Since the E3 region is dispensable from the adenovirus genome (Jones and Shenk, 1978), the current adenovirus vectors, with the help of 293 cells, generally carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, up to about 7.5 kb of foreign DNA may be packaged in an adenovirus. Additionally, modified adenoviral vectors are now available which have an even greater capacity to carry foreign DNA.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a preferred helper cell line is 293. Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) are employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the preference that the adenovirus vector be replication-defective, or at least conditionally defective, the nature of the adenovirus vector is not believed to be critical to the successful practice of the invention. The adenovirus may be selected from any of the 42 different known serotypes or subgroups A–F. Adenovirus serotype 5 of subgroup C is a preferred starting material for obtaining a conditional replication-defective adenovirus vector for use in the present invention. This is, in part, because Adenovirus type 5 is a human adenovirus about which a great deal of biochemical and genetic information is known, and it has historically been used for most constructions employing adenovirus as a vector. Additionally, various modifications can be made to adenovirus to facilitate cell targeting of the expression cassette and/or otherwise modify vector interaction with the host cell. By way of illustration, it is known that primary fibroblasts generally express low levels of the high-affinity Coxsackie virus and Adenovirus receptor (CAR), which receptor facilitates transduction of host cells by the adenoviral vector. However, it is also known that adenoviral vectors can be modified, for example by altering the adenovirus fiber, to improve binding to other cell-surface receptors where CAR receptors are limited (see, e.g. Hidaka et al., 1999).

As stated above, a preferred adenoviral vector according to the present invention lacks an adenovirus E1 region and thus, is replication defective. Typically, it is most convenient to introduce the polynucleotide encoding the gene of interest at the position from which the E1-coding sequences have been removed. However, the position of insertion of the construct within the adenovirus sequences is not critical to the invention. Further, other adenoviral sequences may be deleted and/or inactivated in addition to or in lieu of the E1 region. For example, the E2 and E4 regions are both necessary for adenoviral replication and thus may be modified to render an adenovirus vector replication-defective, in which case a helper cell line or helper virus complex may employed to provide such deleted/inactivated genes in trans. The polynucleotide encoding the gene of interest may alternatively be inserted in lieu of a deleted E3 region, such as in E3 replacement vectors as described by Karlsson et al. (1986), or in the E4 region where a helper cell line or helper virus complements an E4 defect. Other modifications are known to those of skill in the art and are likewise contemplated herein.

Adenovirus is easy to grow and manipulate and exhibits broad host range in vitro and in vivo. This group of viruses can be obtained in high titers, e.g., $10^9$–$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Animal studies initially suggested that recombinant adenovirus could be useful for gene therapy (see, e.g., Stratford-Perricaudet and Perricaudet, 1991; Stratford-Perricaudet et al., 1990; Rich et al., 1993). Studies in administering recombinant adenovirus to different tissues include administration via intracoronary catheter into one or more coronary arteries of the heart (Hammond, et al., 1984), U.S. Pat. Nos. 5,792,453 and 6,100,242), trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is generally employed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989).

Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., (1991) recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct is delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Non-viral methods for the transfer of expression constructs into mammalian cells can also be used in the context of the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention, a naked DNA expression construct may be transferred into cells using particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be complexed with one or more lipid components and/or entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in most eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

III. MEK5 Peptides and Polypeptides

The present invention also provides exemplary MEK5 protein/polypeptide sequences. For example, SEQ ID NO:2 provides a full-length amino acid sequence for MEK5. In addition to the entire MEK5 molecule, the present invention also relates to fragments of the polypeptide that may or may not retain the various functions described below. Fragments, including the N-terminus of the molecule may be generated by genetic engineering of translation stop sites within the coding region (discussed below). Alternatively, treatment of the polypeptides with proteolytic enzymes, known as proteases, can produces a variety of N-terminal, C-terminal and internal fragments. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Structural-Functional Aspects

MEK5 is a MAP family kinase that directly regulates BMK1 activity. It binds MEKK3, which appears to activate MEK5. MEKK2 also has been shown to activated MEK5. The MAPKK, MEK5, was isolated by degenerate PCR and encodes a 444-amino acid protein (49 kD), which has aproximately 40% identity to known MEKs (English et al., 1995; Zhou et al., 1995). The Raf-1 phosphorylation and activation motif of MEK1, $S^{218}XXXS^{222}$ is also conserved as $S^{311}XXXT^{315}$ in MEK5, suggesting a similar regulatory mechanism. The most divergent region among the MEKs is upstream of kinase subdomain I. MEK5 is distinct from other MEKs in that it contains a long N-terminal sequence. A data bank search with the first 150 residues of MEK5 revealed sequence identitiy with two proteins that have important roles in cell division, mating and morphogenesis: the *S. cerevisia* protein CDC24 and the homologous protein from *S. pombe*, scd1. Genetic and biochemical studies have demonstrated that CDC24 has GDP release activity and can bind to the GTPase encoded by CDC42 and enhance GTP/GDP exchange. The mammalian equivalent of yeast CDC42 is Rac, a small GTP-binding protein that is known to regulate actin dynamics.

The mechanism of MEK5 induced eccentric hypertrophy is not known, however, some insight is provided by studies in cultured neonatal rat cardiomyocytes with constitutively active (MEK5DD) and dominant negative (MEK5KM) adenovirses (Nicol et al., 2001). Infection of cardiomyocytes with MEK5DD results in a dramatic elongation of these cells and a concomitant assembly of sarcomeres in series. The change in cell shape and sarcomere assembly induced by MEK5DD in cultured cardiomyocytes is similar the changes that individual myocytes undergo during eccentric hypertrophy of the myocardium and suggests that the signaling pathways regulating concentric and eccentric hypertrophy of cardiomyocytes can be studied in vitro. The phenotype induced by MEK5DD in cultured cardiomyctes is highly unique and to our knowledge is only induced by the IL-6 family cytokines, leukemia inhibitory factor (LIF) and cardiotrophin-1 (CT-1). The inventors decided to test if MEK5 could be operating downstream of LIF to regulate serial assembly of sarcomeres in cardiomyocytes. The results showed that dominant negative MEK5 could block cellular elongation and serial assembly of sarcomeres induced by LIF, but had only a slight effect on parallel assembly of sarcomeres induced by the $\alpha_1$-adrenergic receptor agonist, phenylephrine. Therefore, MEK5 seems to have a highly specific role in regulating the balance between serial and parallel assembly of sarcomeres.

B. Variants of MEK5

Mutations in activating phosphorylation sites and the conserved lysine residues in the ATP binding site of MEK1 result in dominant negative mutants that can interfere with the kinase function (Cowley et al., 1994; Seger et al., 1994; Mansour et al., 1994). Similar results were found with the MEK5 dominant negative mutants, S311A/T315A and K195M (MEK5KM) (Zhou et al., 1995). Substitution of the conserved phosphorylation sites of MEK1 with acidic residues such as aspartate or glutamic acid has been shown to generate a constitutively active kinase (Cowley et al., 1994; Seger et al, 1994; Mansour et al., 1994), and this principle was used to generate the consitutively active MEK5 mutant, S311D/T315D (MEK5DD) (Kato et al., 1997). Thus, it is contemplated that a number of different MEK5 variants may prove useful.

Amino acid sequence variants of a MEK5 polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MEK5, but with altered and even improved characteristics.

C. Domain Switching

Domain switching involves the generation of chimeric molecules using different but, in this case, related polypeptides. By comparing various MEK5 proteins, one can make predictions as to the functionally significant regions of these molecules. It is possible, then, to switch related domains of these molecules in an effort to determine the criticality of these regions to MEK5 function. These molecules may have additional value in that these "chimeras" can be distinguished from natural molecules, while possibly providing the same function.

D. Fusion Proteins

A specialized kind of insertional variant is the fusion protein. This molecule generally has all or a substantial portion of the native molecule linked, at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

E. Purification of Proteins

It may be desirable to purify MEK5 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthetic Peptides

The present invention also includes smaller MEK5-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

G. Antigen Compositions

The present invention also provides for the use of MEK5 proteins or peptides as antigens for the immunization of animals relating to the production of antibodies. It is envisioned that MEK5 or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

IV. Generating Antibodies Reactive With MEK5

In another aspect, the present invention contemplates an antibody that is immunoreactive with a MEK5 molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988). The genes for MEK5 monoclonal antibodies can be utilized, usually as single-chain contructs, as inhibitors of MEK5 function.

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to MEK5-related antigen epitopes. Additionally, it is proposed that monoclonal antibodies specific to the particular MEK5 of different species may be utilized in other useful applications In general, both polyclonal and monoclonal antibodies against MEK5 may be used in a variety of embodiments. For example, they may be employed in antibody cloning protocols to obtain cDNAs or genes encoding other MEK5s. They may also be used in inhibition studies to analyze the effects of MEK5-related peptides in cells or animals. MEK5 antibodies will also be useful in immunolocalization studies to analyze the distribution of MEK5s during various cellular events, for example, to determine the cellular or tissue-specific distribution of MEK5 polypeptides at different points in the cell cycle. A particularly useful application of such antibodies is in purifying native or recombinant MEK5, for example, using an antibody affinity column. The operation of such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MCIP protein, polypeptide or peptide or cell expressing high levels of MCIP. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

V. Inhibition of Cardiac Hypertrophy and Dilated Cardiomyopathy

A. Gene Therapy

One skilled in the art recognizes that various methods of DNA delivery may be employed to deliver the polynucleotides of the present invention to specific cells for gene therapy. Further, in the context of gene therapy, a skilled artisan is cognizant that the vector to be utilized will generally contain the gene of interest operatively linked to a promoter. One skilled in the art also recognizes that, in certain instances, other sequences such as a 5' and/or 3'-UTR regulatory sequences are useful in expressing the gene of interest.

Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed release of the composition. Alternatively or additionally, the composition may be targeted by the delivery itself, for example by intracoronary delivery to target the heart (see e.g. U.S. Pat. Nos. 5,792,453 and 6,100,242, hereby incorporated by reference in their entirety). A pharmaceutically acceptable form should be employed which does not deactivate the compositions of the present invention. In pharmaceutical dosage forms, the compositions can be used alone or in appropriate association, as well as in combination, with other pharmaceutically active compounds. Preferably, a sufficient amount of vector containing the therapeutice nucleic acid sequence is administered to provide a pharmacologically effective dose of the gene product, for example to alleviate symptoms associated with the disease being treated.

One skilled in the art recognizes that other methods of delivery may likewise be utilized to administer an expression cassette into a cell. Examples include: (1) methods utilizing physical means, such as electroporation (electricity), a gene gun (physical force) or applying large volumes of a liquid (pressure); and (2) methods wherein said expression cassette is complexed with another entity, such as a lipid-based vector (e.g., a liposome), an aggregated protein or a transporter molecule. Certain of these embodiments are primarily suitable for ex vivo applications.

The actual dose and schedule can vary, for example, depending on whether the compositions are administered in combination with other pharmaceutical compositions, or depending on inter-individual differences in pharmacokinetics, drug disposition, and metabolism. Similarly, amounts to be administered can vary in in vitro applications, for example depending on the particular cell line utilized (e.g., based on the variable number and/or type of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as the nature of the sequence itself. Thus, vector amount is particularly a parameter which is preferably determined empirically and can be altered due to factors not inherent to the present invention (for instance, the cost associated with synthesis). One skilled in the art can easily make adjustments to dose in accordance with the exigencies of the particular situation.

Those of skill in the art are well aware of how to apply gene delivery to in vivo situations. By way of illustration, for viral vectors, one generally will prepare a viral vector stock. Depending on the type of virus utilized and the titer attainable, one will generally deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ to $10^{13}$ infectious particles to the patient. Similar figures may be extrapolated for lipid-based or other non-viral formulations by comparing relative uptake efficiencies. Formulation as a pharmaceutically acceptable composition is discussed further below. Various routes are contemplated, but local provision to the heart, preferably by the method of Hammond et al., supra and intra-arterial or intravenous administration are preferred.

It is contemplated that blocking MEK5 activity will prevent cardiac cell elongation, which in turn will prevent dilated cardiomyopathy and/or cardiac hypertrophy. This may be accomplished in one of several ways. First, one may provide an analog of MEK5's target that binds and inhibits MEK5 function, effectively creating a "suicide substrate" for MEK5. This approach also could be exploited using a mimetic (see above). Second, one could use a similar peptide target, with an additional domain capable of cleaving MEK5. Third, one could provide a non-functional MEK5 analog that is capable of competing with MEK5 peptide. And fourth, small molecule, antisense or ribozyme techniques could also be used to inhibit the expression of MEK5.

B. Combined Therapy

In another embodiment, it is envisioned to use MEK5 inhibition in combination with other therapeutic modalities. Thus, in addition to the therapies described above, one may also provide to the patient more "standard" pharmaceutical cardiac therapies. Examples of standard therapies include, without limitation, so-called "beta blockers", anti-hypertensives, cardiotonics, anti-thrombotics, vasodilators, hormone antagonists, endothelin antagonists, calcium channel blockers, phosphodiesterase inhibitors, angiotensin type 2 antagonists and cytokine blockers/inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, MEK5 inhibition may precede or follow administration of the other agent by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a MEK5 inhibitor, or the other agent will be desired. In this regard, various combinations may be employed. By way of illustration, where the MEK5 inhibitor is "A" and the other agent is "B", the following permutations based on 3 and 4 total administrations are exemplary:

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well know in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy

| A/B/A | B/A/B | B/B/A | A/A/B | B/A/A | A/B/B | B/B/B/A | B/B/A/B |
|---|---|---|---|---|---|---|---|
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are likewise contemplated.

VI. Drug Formulations and Routes for Administration to Patients

Where clinical applications are contemplated, pharmaceutical compositions will be prepared—e.g., expression vectors, virus stocks and drugs—in a form appropriate for the intended application. Generally, this will entail preparing compositions that are essentially free of pyrogens, as well as other impurities that could be harmful to humans or animals.

syringability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580).

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VII. Methods of Making Transgenic Mice

A particular embodiment of the present invention provides transgenic animals that contain MEK5-related constructs. Transgenic animals expressing MEK5, antisense MEK5, dominant negative MEK5, or activated MEK5, recombinant cell lines derived from such animals, and transgenic embryos may be useful in determining the exact role that MEK5 plays in the development and differentiation of cardiomyocytes. Furthermore, these transgenic animals may provide an insight into heart development. The use of constitutively expressed MEK5 provides a model for over- or unregulated expression. Also, transgenic animals which are "knocked out" for MEK5, in one or both alleles are contemplated.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. (1985); which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press (1994); which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. (1986), in Palmiter et al. (1982); in *The Qiagenologist, Application Protocols,* 3rd edition, published by Qiagen, Inc., Chatsworth, Calif.; and in Sambrook et al. (1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

VIII. Screening Assays

The present invention also contemplates the screening of compounds for various abilities to interact with and/or affect MEK5 expression or function. Particularly preferred compounds will be those useful in inhibiting the actions of MEK5 in regulating gene expression in cardiomyocytes. In the screening assays of the present invention, the candidate substance may first be screened for basic biochemical activity—e.g., binding to a target molecule, inhibition of expression of a target molecule—and then tested for its ability to inhibit modulate activity, at the cellular, tissue or whole animal level.

A. Modulators and Assay Formats i) Assay Formats

The present invention provides methods of screening for modulators of MEK5 expression and binding to MEK5. In one embodiment, the present invention is directed to a method of:

(a) providing a MEK5 polypeptide;

(b) contacting the MEK5 polypeptide with the candidate substance; and (c) determining the binding of the candidate substance to MEK5 polypeptide.

In yet another embodiment, the assay looks not at binding, but at MEK5 function. Such methods would comprise, for example:

(a) providing MEK5 to a cell;

(b) contacting the cell with a candidate modulator; and (c) measuring the effect of the candidate substance on the function of MEK5.

Clearly, two such functions are MEK5 kinase activity and MEK5-induced transcription. A related assay that examines the expression of MEK5 would comprise:

(a) providing a cell that expresses MEK5;

(b) contacting said cell with a candidate substance; and (c) measuring the effect of the candidate substance on MEK5 expression.

Measuring expression can be performed by examining mRNA expression, although alterations in mRNA stability and translation would not be accounted for. A more direct way of assessing expression is by directly examining protein levels, for example, through Western blot or ELISA.

ii) Inhibitors and Activators

An inhibitor according to the present invention may be one which exerts an inhibitory effect on the expression or function of MEK5. By the same token, an activator according to the present invention may be one which exerts a stimulatory effect on the expression or function of MEK5.

iii) Candidate Substances

As used herein, the term "candidate substance" refers to any molecule that may potentially modulate MEK5 expression or function. The candidate substance may be a protein or fragment thereof, a small molecule inhibitor, or even a nucleic acid molecule. It may prove to be the case that the most useful pharmacological compounds will be compounds that are structurally related to compounds which interact naturally with MEK5. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like MEK5, and then design a molecule for its ability to interact with MEK5. Alternatively, one could design a partially functional fragment of MEK5 (binding, but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of hypertrophic response.

Other suitable inhibitors include small molecules, antisense molecules, ribozymes, and antibodies (including single chain antibodies). It will, of course, be understood that the screening methods of the present invention are useful in themselves notwithstanding the fact that effective candidates may not be found. The invention provides methods for screening for such candidates, not solely methods of finding them.

B. In Vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays.

In one embodiment of this kind, the screening of compounds that bind to a MEK5 molecule or fragment thereof is provided The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as MEK5). Competitive binding assays can be performed in which one of the agents (MEK5 for example) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, MEK5 and washed. Bound polypeptide is detected by various methods.

Purified target, such as MEK5, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region (e.g., the C-terminus of MEK5) to a solid phase.

C. In Cyto Assays

Various cell lines that express MEK5 can be utilized for screening of candidate substances. For example, cells containing MEK5 with an engineered indicators can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (growth, size, Ca-++ effects). Alternatively, molecular analysis may be performed in which the function of MEK5 and related pathways may be explored. This involves assays such as those for protein expression, enzyme function, substrate utilization, mRNA expression (including differential display of whole cell or polyA RNA) and others.

D. In Vivo Assays

The present invention particularly contemplates the use of various animal models. Transgenic animals may be created with constructs that permit MEK5 expression and activity to be regulated and monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

E. Production of Inhibitors

In an extension of any of the previously described screening assays, the present invention also provide for methods of producing inhibitors. The methods comprising any of the preceding screening steps followed by an additional step of "producing the candidate substance identified as a modulator of" the screened activity.

X. Examples

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Immunoprecipitation, Kinase Assays, and Immunoblotting

Immunoprecipitations (IPs) and kinase assays were performed as described (English et al., 1999b). Substrates used were glutathione-S-transferase (GST) fused to MEF2C amino acids 204–321 or GST-ERK5KM$\Delta$, a truncated, catalytically inactive form of ERK5 with lysine-83 mutated to methionine. Following incubation for 30 min at 30° C., samples were separated by SDS-PAGE and transferred to a polyvinylidene difluoride (PVDF) membrane. The level of $^{32}$P-labeled GST-fusion protein on the membrane was analyzed using a Phosphor Imager (Molecular Dynamics). The membrane was then immunoblotted with anti-ERK5 rabbit polyclonal antibody (StressGen) at a final concentration of 150 ng/ml and proteins were visualized using a chemiluminescence system (Santa Cruz). Other antibodies were used at the following concentrations or dilutions for immunoblotting: anti-HA high affinity rat monoclonal antibody (Roche)

50 ng/ml; anti-MEK5 mouse monoclonal M72220 (Transduction Laboratories) 250 ng/ml; anti-MEK5 rabbit polyclonal L610 (English et al., 1995) 1:500.

Construction of Adenoviruses and other DNA Constructs

All constructs were generated from cDNAs encoding the MEK5β splice isoform (English et al., 1995). MEK5 mutants have been described previously (English et al., 1999b). MEK5 cDNAs were HA-tagged by polymerase chain reaction (PCR) and cloned into the vector pAC-CMV. Recombinant adenoviruses were generated by co-transfection of pAC-CMV constructs along with pJM17 into 293 cells using the calcium phosphate precipitation method (Becker et al., 1994). Primary lysates were amplified by reinfection of 293 cells. Titering of viruses was performed on 293 monolayers using the agar overlay method. Titers were in the range of $0.5-1\times10^9$ plaque forming units (pfu)/ml. The Ad-MEK1CA and β-galactosidase adenoviruses were a gift from L. J. Klesse and L. F. Parada (Klesse et al., 1999).

Cardiomyocyte Culture

Cardiomyocyte cultures were prepared by dissociation of 1-day-old neonatal rat hearts and were differentially plated to remove fibroblasts. Cells were plated in 4:1 DMEM:199 media with 10% horse serum and 5% fetal calf serum at a density of $5\times10^4$ cells/cm$^2$ for immunofluorescence experiments and at a density of $2\times10^4$ cells/cm$^2$ for RNA and kinase experiments. Eighteen hours after plating, cells were changed into serum-free media and either incubated for an additional forty-eight hours prior to treatment with hypertrophic agents or infected with adenovirus at a multiplicity of infection of 100. In cases where adenovirus-infected cells were treated with LIF or PE, these agents were added 24 hr after the initial adenovirus infection. Treatment with hypertrophic agents was continued for 24 hours in cases where RNA was harvested and for 48 hours in cases where cells were fixed for immunostaining.

Immunofluorescence

For immunofluorescence, cells were grown on glass coverslips coated with 4 μg/cm$^2$ laminin (Gibco-BRL). Cells were fixed in 3.7% formaldehyde on ice for 30 min, permeabilized with 0.1% Triton-X 100 in PBS, and blocked with 5% serum in PBS for 1 hr at room temperature. Cells were incubated with monoclonal anti-α-actinin (sarcomeric) clone EA-53 (Sigma) at a dilution of 1:40 in blocking buffer for 1 hr at 37° C., washed, and incubated with fluorescein-conjugated horse anti-mouse IgG antibody (Vector) at a dilution of 1:200 in blocking buffer for 1 hour at 37° C. Following secondary antibody incubation, cells were washed with PBS and rinsed briefly with 2 μg/ml Hoechst in H$_2$O.

Transgenic Mice and Genotyping

An expression plasmid encoding a constitutively active form of MEK5□ (MEK5DD) was subcloned into pBluescript between the α-myosin heavy chain promoter and the human growth hormone poly-A tail (Gulick et al., 1991). The MEK5DD sequence was preceded by an HA-epitope tag. Plasmid DNA was removed by NotI digestion, and the linearized MEK5DD construct was gel-purified.

(C3HB6)$_{F1}$ mice were superovulated by standard procedures and fertilized eggs were injected with linearized DNA (2 ng/μl). Injected eggs were transferred to the oviducts of pseudopregnant ICR mice. Offspring were analyzed for the presence of the transgene by Southern analysis of genomic DNA using a $^{32}$P-labeled human growth hormone cDNA fragment as a probe.

Transthoracic Echocardiography

Cardiac function of wildtype and MEK5-transgenic mice was evaluated noninvasively by transthoracic echocardiography. Mice at the age of 6–10 wks were anaesthetized with 2.5% Avertin (15 μl/g body weight). The ventral chest was shaved and the animal placed on a thermally-controlled table in a slight left lateral decubitus position. Echocardiography was performed using a Hewlett Packard (Andover, Mass.) Sonos 5500 Ultrasound system with a 12 Mhz transducer. Heart rate was determined by electrocardiogram analysis. At least three independent M-mode measurements per animal were obtained by an examiner blinded to the genotype of the animal. End systolic and end diastolic chamber diameter, interventricular septum and posterior wall thickness, as well as left ventricular fractional shortening (FS%=[(LVEDD−LVESD)/LVEDD]×100), were determined in a short axis view at the level of the papillary muscles.

Histology and Morphometric Analysis

Hearts from wildtype and transgenic mice were collected, fixed in 10% formalin buffered with PBS, dehydrated in ethanol, transferred to xylene, and then to paraffin. Paraffin-embedded hearts were sectioned at 4 μm and subsequently stained with hematoxylin and eosin or with Masson trichrome. Myocyte cross-sectional areas were measured from wildtype and MEK5DD-transgenic heart sections (n=10) using a computerized morphometric system (Scion Image, National Institutes of Health). Sections from different regions of the heart (left and right ventricle, septum, and papillary muscle) were measured at a 40× magnification. Myocyte cross-sectional area was measured per nucleus and only myocytes that were cut in the same direction were included in the measurements. As criteria, the position and shape of the nucleus within the myocyte were used. The same software was used to quantitate area, perimeter, and major and minor axis of cardiomyocytes grown on coverslips.

RNA Isolation and Dot Blot Analysis

Total RNA was purified with Trizol reagent (GIBCO BRL) as recommended. RNA from wildtype and transgenic hearts, as well as from cultured cardiomyocytes, was subjected to dot blot hybridization against a panel of oligonucleotide probes as described (Jones et al., 1996).

Example 2

Results

Activation of ERK5 by Hypertrophic Agents and Stress

Previous studies showed that ERK5 is strongly activated by ischemia in vivo, as well as oxidative and osmotic stress in cultured cells (Abe et al., 1996; Takeishi et al, 1999). This pathway has also been shown to be activated by signaling through the Gα$_q$ and G$_{12/13}$ families of heterotrimeric G-proteins in fibroblasts (Fukuhara et al., 2000). To determine if ERK5 might be a target of hypertrophic signaling pathways in cardiomyocytes, the inventors treated primary neonatal rat cardiomyoctyes with the hypertrophic agonists, phenylephrine (PE) and LIF, and the stress agents, $H_2O_2$ and sorbitol (FIG. 1). Following treatment, cardiomyocytes were harvested and ERK5 immunoprecipitation (IP) kinase assays were performed with a GST-MEF2C substrate. Phosphorylation of GST-MEF2C indicated that ERK5 was activated 2–4 fold by hypertrophic agents, with activation peaking at about 10 min and declining to basal levels or below by 60 min (FIGS. 1A and B). As shown previously (Abe et al., 1996), sorbitol gave a strong sustained activation of ERK5 (8-fold at 60 min), while $H_2O_2$ gave a lower but also sustained activation (5-fold at 60 min) (FIGS. 1C and D). Western blotting of immunoprecipitates with anti-ERK5 antibody showed that equivalent amounts of ERK5 protein were present in the kinase reactions (FIGS. 1A–D). The endogenous ERK5 protein migrates at approximately 100 kDa on SDS-PAGE and phosphorylation of the protein has been shown to produce an upward shift in mobility. The inventors did not observe this mobility shift in all of our experiments, probably because only a small percentage of the total protein was activated (FIGS. 1A–D).

Activated MEK5 Induces Serial Assembly of Sarcomeres In Vitro

The inventors next investigated the outcome of ERK5 activation in cardiomyoctyes using adenoviruses expressing three different forms of MEK5: wild-type MEK5 (AdMEK5WT), activated MEK5 (AdMEK5DD) with aspartate substitutions of serine-222 and threonine-226, and dominant negative MEK5 (AdMEK5KM) with a methionine substitution of ATP-binding lysine-106 (English et al., 1999b). All three MEK5 derivatives were tagged with an HA epitope.

Initially, the viruses were used to infect COS cells. Western blotting and IP kinase assays with anti-HA antibody and ERK5 kinase-dead substrate confirmed that the viruses expressed proteins of the correct size and that AdMEK5DD produced a constitutively active kinase (FIGS. 2A and B). Some kinase activity was also observed with the AdMEK5WT virus (FIG. 2B). The viruses were then used to infect neonatal rat cardiomyocytes. Following infection, cells were serum-starved for 72 hours, fixed, and stained with anti-sarcomeric α-actinin antibody (FIGS. 2C–H). Adenoviruses expressing β-galactosidase (Adβ-gal) and an activated form of MEK1 (AdMEK1CA) were used for comparison. Control cells infected with Adβ-gal lacked well-developed sarcomeres (FIG. 2C). Cells infected with AdMEK1CA or treated with PE had well-assembled sarcomeric structures, an angular appearance, and increased cell area (FIGS. 2D and F, and Table 4). Surprisingly, cardiomyocytes infected with AdMEK5DD were highly elongated (FIG. 2E) when compared to either AdMEK1CA-infected cardiomyocytes or cardiomyoctyes treated with PE for 48 hrs (FIGS. 2D and F). Although the average length of AdMEK5DD-infected cardiomyocytes was similar to the average length of AdMEK1CA infected-cardiomyocytes, this increase in length occurred without a corresponding increase in cell width, thus producing a 2-fold increase in average length to width ratio (Table 4). In spite of their unusual elongated appearance, MEK5DD-expressing cardiomyocytes exhibited assembled sarcomeric structures comparable to those seen in PE-treated cells (FIGS. 2G and H).

TABLE 4

Morphometric analysis of cardiomyocytes

| Cell Treatment | Area ($\mu m^2$) | Major axis ($\mu m$) | Minor axis ($\mu m$) | Major/Minor |
|---|---|---|---|---|
| Adβ-gal | 2167 ± 688 | 65 ± 11 | 42 ± 9.1 | 1.58 ± 0.39 |
| AdMEK1CA | 7146 ± 1560 | 134 ± 22 | 68 ± 12 | 2.38 ± 1.03** |
| AdMEK5DD | 3440 ± 1050 | 136 ± 37** | 34 ± 13** | 4.65 ± 2.28** |
| PE | 5745 ± 1560 | 110 ± 20 | 66 ± 12 | 1.71 ± 0.37 |
| PE + Adβ-gal | 6411 ± 2070 | 122 ± 23 | 66 ± 13 | 1.91 ± 0.44 |
| PE + AdMEK5KM | 4524 ± 1140* | 98 ± 15 | 59 ± 10 | 1.71 ± 0.35 |
| LIF | 3586 ± 1090 | 144 ± 36** | 33 ± 12** | 5.06 ± 2.35** |
| LIF + Adβ-gal | 3671 ± 874 | 148 ± 42** | 35 ± 14** | 5.37 ± 3.26** |
| LiF + AdMEK5KM | 4683 ± 889‡ | 101 ± 16‡ | 59 ± 10‡ | 1.78 ± 0.47‡ |

Figure 2:
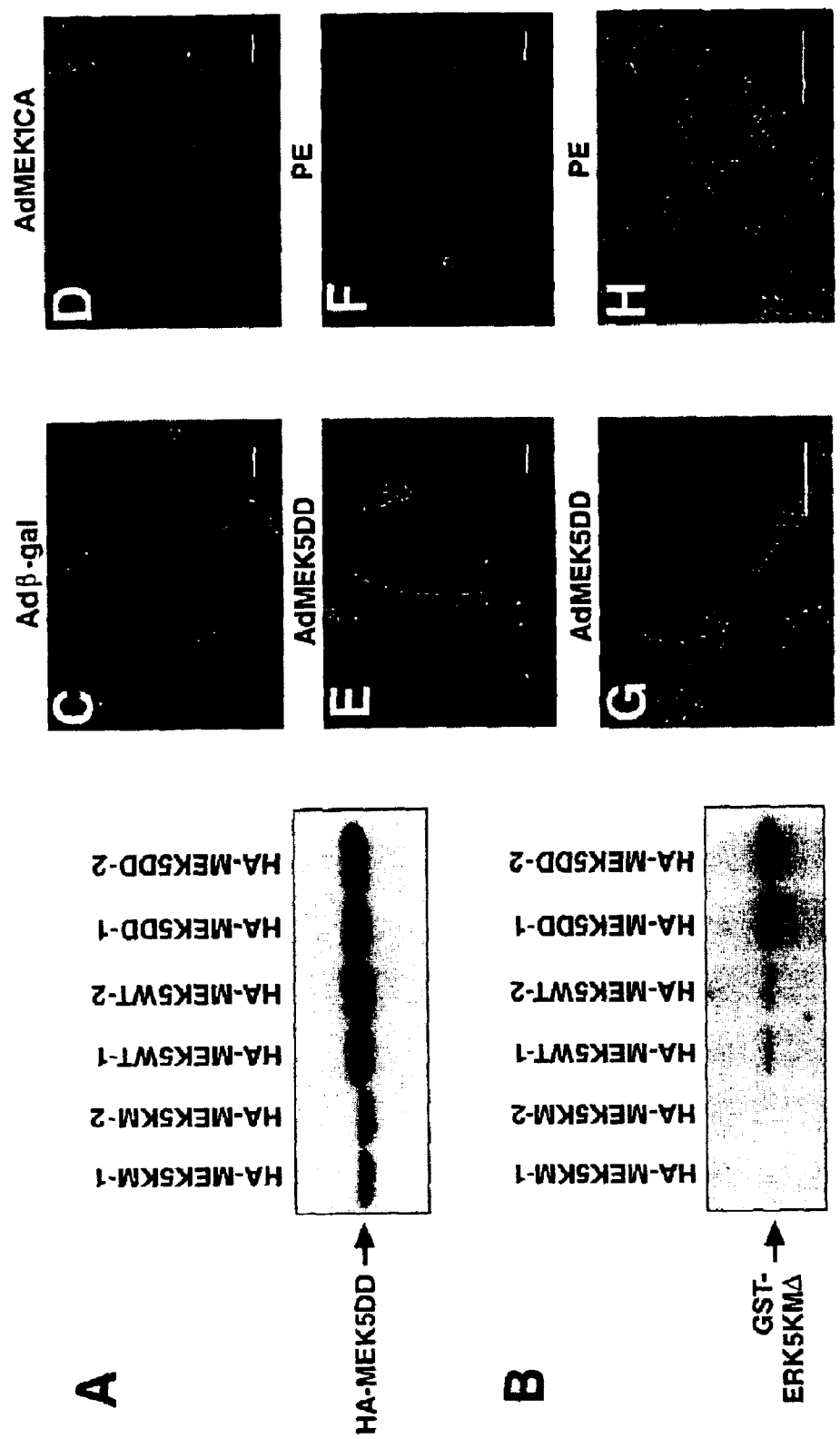
FIGS. 2A–H. Activated MEK5 induces elongation of cultured neonatal rat cardiomyocytes. Adenoviruses expressing HA-tagged MEK5KM, MEK5WT, and MEK5DD were used to infect COS cells at an moi of 100.
Figure 3:
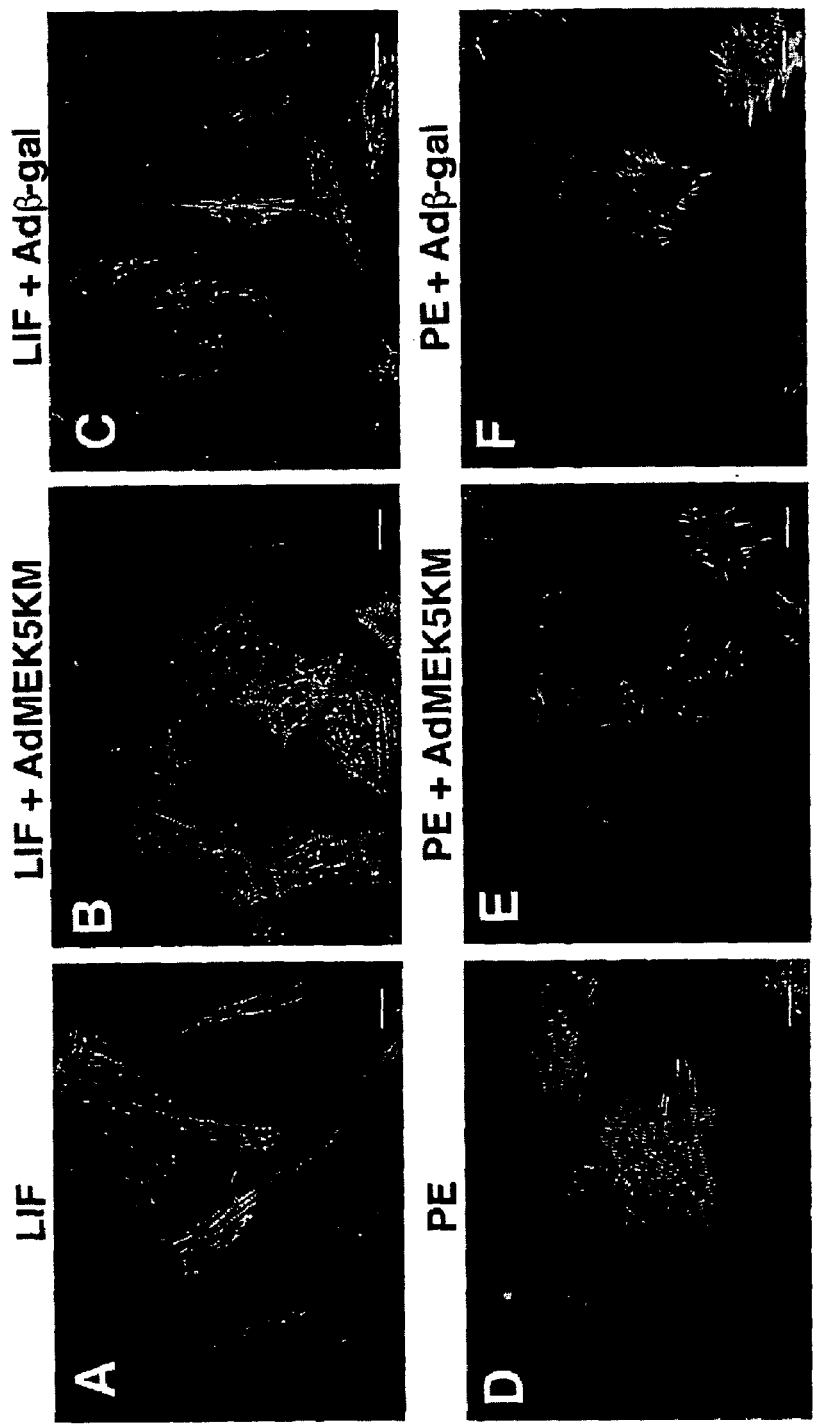
FIGS. 3A–F. Dominant negative MEK5 blocks LIF-induced elongation of neonatal rat cardiomyocytes. Cardiomyocytes were either not infected or infected with adenovirus at an moi of 100, serum-deprived, and 24 hours post-infection treated either with LIF (1000 units/ml) or PE (50 μM) for an additional 48 hrs prior to fixation and immunostaining with anti-sarcomeric α-actinin.

Neonatal rat cardiomyocytes were infected with virus and treated with PE (100 $\mu$M) or LIF (1000 units/ml) where indicated and as described in legends for FIGS. 2 and 3. Measurements were made using a computerized morphometric system. Thirty cells were examined for each adenovirus, and this was repeated for 3 independent experiments. Values are mean ± SD;
*, $p < 0.05$ versus PE treated (no virus);
**, $p < 0.001$ versus PE treated (no virus);
‡, $p < 0.001$ versus LIF treated (no virus).

Dominant Negative MEK5 Blocks LIF-Induced Hypertrophy

The elongated phenotype of MEK5DD-expressing cardiomyocytes was reminiscent of the phenotype induced by the cytokines, CT-1 and LIF (Wollert et al., 1996). To determine if MEK5 might participate in a LIF-activated signaling pathway that mediates serial assembly of sarcomeres, the inventors infected cardiomyoctyes with β-gal- and MEK5KM-expressing adenoviruses and analyzed the effects of LIF on these cells and on uninfected cells (FIGS. 3A–C and Table 4). LIF induced dramatic elongation of uninfected and Adβ-gal-infected cardiomyocytes (FIGS. 3A and 3C and Table 4). In contrast, cells infected with MEK5KM adenovirus failed to undergo LIF-induced elongation (FIG. 3B and Table 4). However, these cardiomyocytes did still exhibit assembled sarcomeres and increased surface area (FIG. 3B and Table 4). Parallel sarcomeric assembly in response to PE occurred in uninfected as well as Adβ-Gal- and AdMEK5KM-infected cells (FIGS. 3D–F), although there was some reduction in total cell surface area in MEK5KM-infected cardiomyocytes (Table 4). Therefore, it appears that MEK5 may be an essential component of a LIF-activated signaling pathway leading to cardiomyocyte elongation and serial assembly of sarcomeres. This result further demonstrates that parallel assembly of sarcomeres induced by LIF and PE does not require MEK5.

Figure 4:
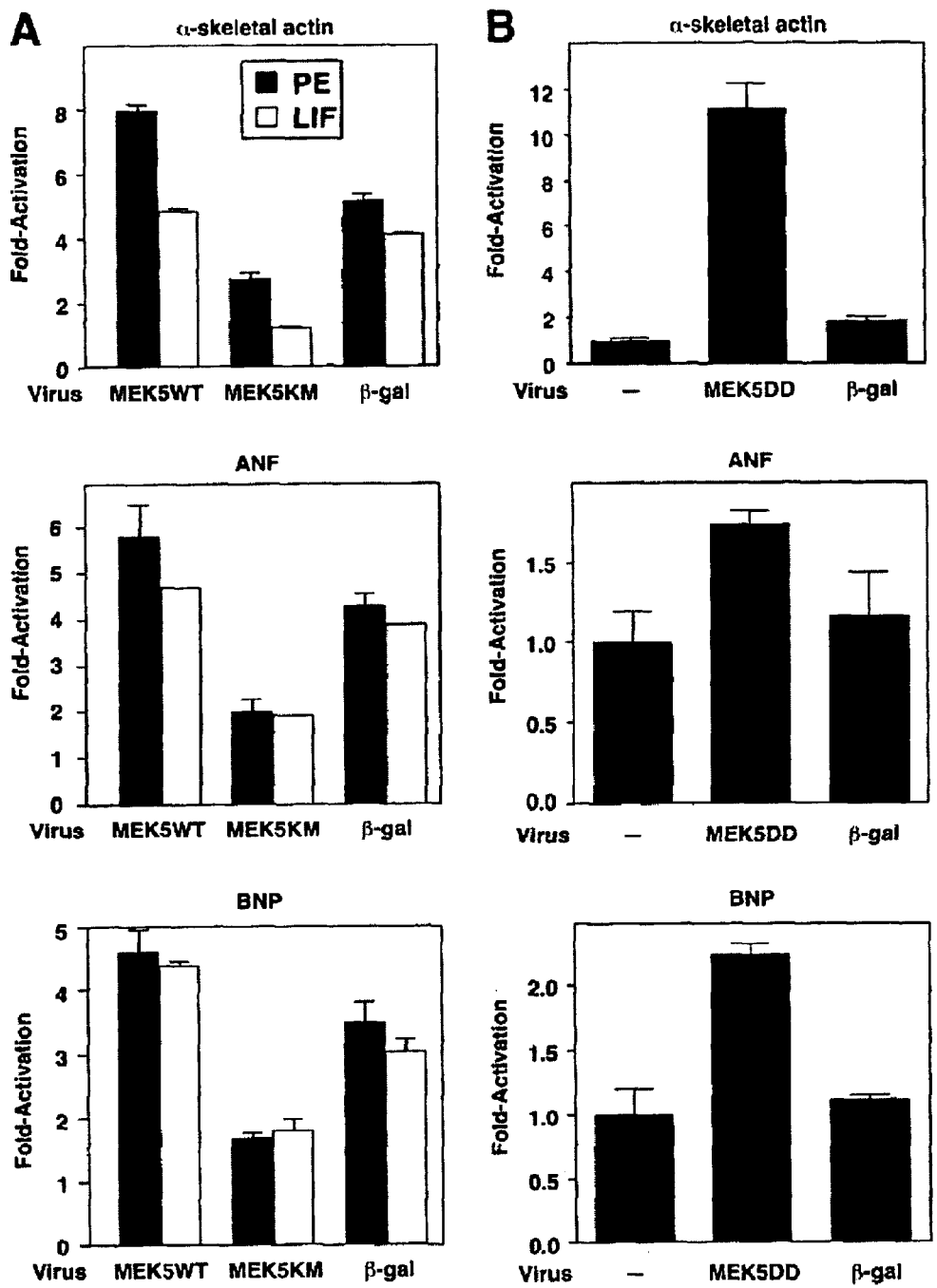
FIGS. 4A–B. MEK5 signaling contributes to the regulation of cardiomyocyte fetal gene expression by PE and LIF.

MEK5 Synergizes with Hypertrophic Signaling Pathways to Induce Fetal Gene Expression To determine whether elevated MEK5 could also transduce signals that regulate fetal gene expression, the inventors treated cardiomyocytes infected with AdMEK5WT, AdMEK5KM or Ad□-gal with LIF or PE and analyzed expression of atrial natriuretic factor (ANF), brain natriuretic peptide (BNP) and skeletal α-actin (FIG. 4A). Skeletal α-actin expression was induced 4- to 5-fold in Adβ-gal-infected cells treated with LIF or PE, and this induction was slightly higher in cells infected with AdMEK5WT (FIG.

4A). Likewise, ANF and BNP expression were induced 3- to 4-fold by both agonists and this induction was even higher in cells infected with AdMEK5WT (FIG. 4A). Agonist induction of all three of these fetal genes was partially or completely blocked by Ad-MEK5KM (FIG. 4A). In the absence of PE or LIF treatment, Ad-MEK5DD had only a slight effect on ANF or BNP expression, however, the constitutively active kinase strongly induced skeletal α-actin expression (FIG. 4B). The control Adβ-gal did not significantly affect fetal gene expression in the presence or absence of agonist.

Activated MEK5 Induces Dilated Cardiomyopathy in Mice

To determine whether activated MEK5 is also capable of inducing cardiomyocyte hypertrophy in vivo, the inventors created transgenic mice that overexpressed MEK5DD in the heart under the control of the α-MHC promoter. The level of transgene expression in five different lines of transgenic mice was determined by anti-HA western blot (FIG. 5A).

Figure 5:
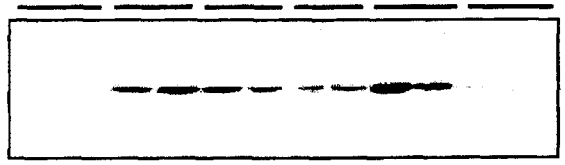
FIGS. 5A–C. Expression of MEK5 and ERK5 in wild-type and MEK5DD-transgenic mice. Lysates were prepared from wild-type (WT) and transgenic (TG) hearts, and 20 ug of protein was separated by SDS-PAGE.
Figure 5:
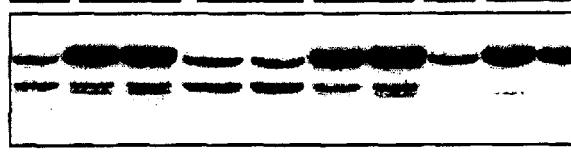
Figure 5:
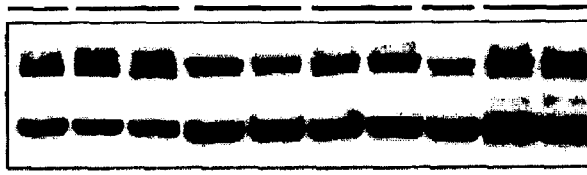

The inventors compared levels of HA-MEK5DD to endogenous MEK5 in wild-type and transgenic mice by anti-MEK5 western blot (FIG. 5B). There are two isoforms of the MEK5 protein, MEK5α and MEK5β, produced by alternative splicing. These proteins are identical except that MEK5α has an 89 amino acid extension at its amino terminus. Because the inventors used MEK5β and mutants thereof for our overexpression studies in cultured cardiomyocytes and transgenic mice, MEK5DD co-migrates with endogenous MEK5β. The inventors found an 8-fold increase in levels of total MEK5β (HA-MEK5DD+endogenous MEK5β) in transgenic animals relative to wild-type and this did not change with age. Endogenous MEK5α expression was unchanged in MEK5DD-transgenic animals (data not shown). Levels of endogenous ERK5 expression were not altered in transgenic hearts relative to wild-type; however, a more slowly migrating band was observed in extracts from transgenic hearts relative to wild-type, particularly in one week-old animals. Presumably the more slowly migrating band represents phospho-ERK5 (FIG. 5C). This suggests that expression of activated MEK5 in transgenic hearts induces phosphorylation of endogenous ERK5.

Figure 6:
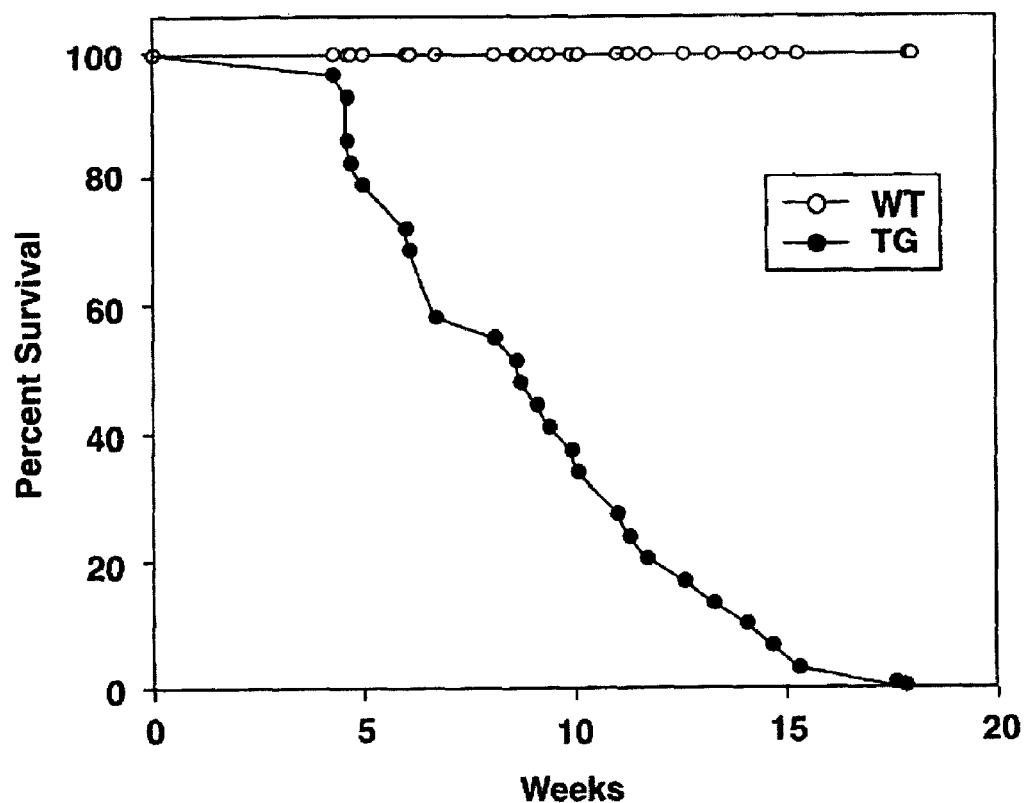
FIG. 6. Survival curve for wild-type and MEK5DD transgenic mice. $F_1$ hemizygous transgenic mice were generated by backcrossing the transgenic founder mouse with C57B6 mice. The open circles represent percent survival of nontransgenic (NTG) $F_1$ mice (n=24); the closed circles represent percent survival of transgenic (TG) $F_1$ mice (n=24).

Transgenic mice appeared normal at birth and thrived, but by 4–5 weeks of age they began to die, apparently from heart failure (FIG. 6). By about 8 weeks of age, approximately half of the transgenic mice had died. Past 8 weeks of age, transgenic mice continued to die prematurely, although some lived as long as 18 weeks.

Figure 7:
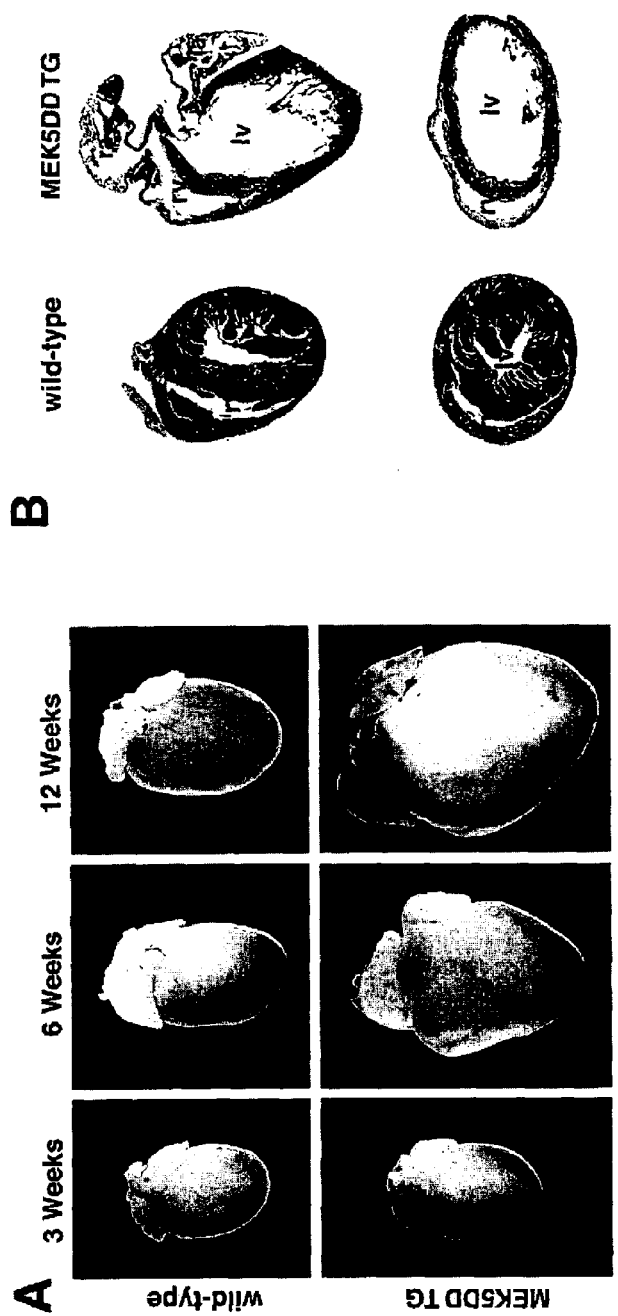
FIGS. 7A–B. MEK5DD-transgenic hearts show progressive dilation and thinning of ventricular walls with age.

At 3 weeks of age, transgenic hearts appeared normal, but by 6 weeks of age many of the transgenic hearts were enlarged (FIG. 7A). Mice that survived until 12 weeks of age showed even more pronounced ventricular dilation. In addition, atrial enlargement and formation of large atrial thrombi was frequently observed. Sectioning of lungs and liver in 8 and 12 week-old mice revealed the presence of congestion (data not shown), suggesting diminished cardiac performance characteristic of congestive heart failure.

Figure 8:
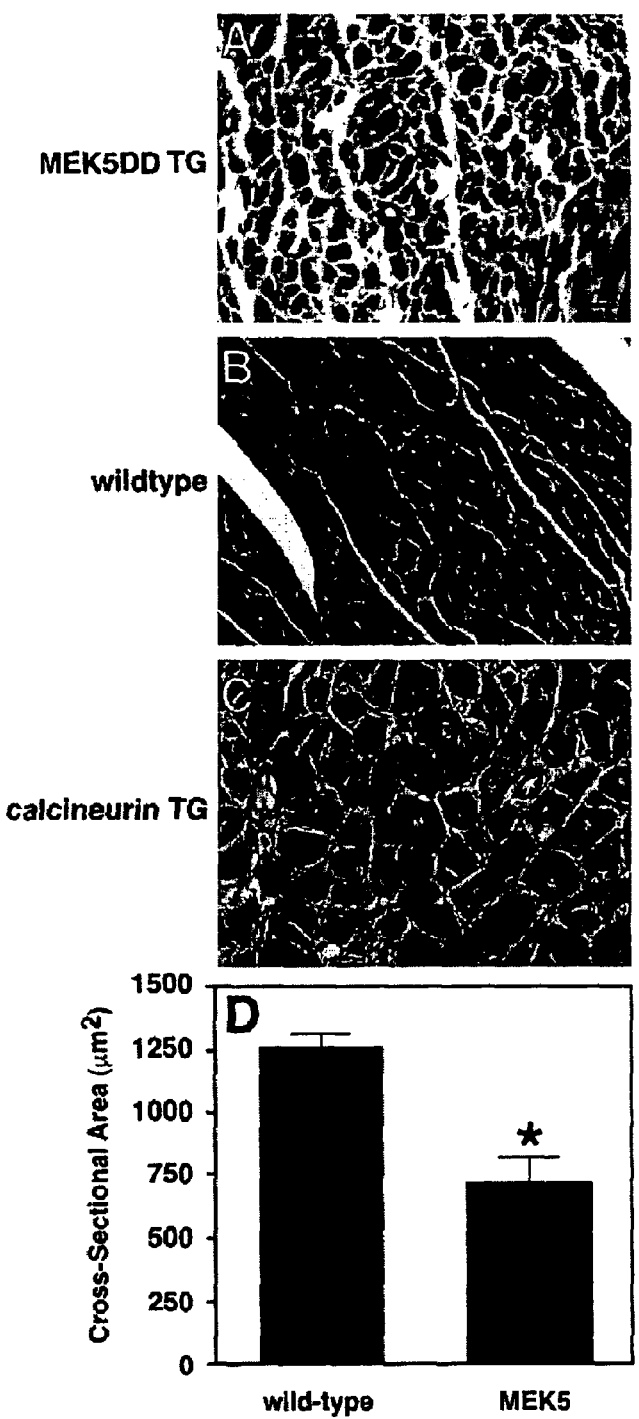
FIGS. 8A-D. MEK5DD-transgenic hearts show reduced myofiber cross-sectional area relative to wild-type. Hearts were removed from 8 week-old wild-type and MEK5DD- and calcineurin-transgenic mice, fixed, sectioned and stained with hematoxylin-eosin. Dramatic differences in myocyte cross-sectional area are apparent in hematoxylin-eosin stained sections from (FIG. 8A) MEK5DD-transgenic hearts, (FIG. 8B) wild-type hearts, and (FIG. 8C) calcineurin-transgenic hearts. Bar=20 μm (FIG. 8D) Cross-sectional area of myocytes from 8 week-old wild-type and MEK5DD-transgenic mice was quantitated using a computerized morphometric system. Measurements were made on equivalent sections from 5 wild-type and 5 transgenic hearts, and within each section, measurements were taken from left and right ventricle, septum, and papillary muscle (10 measurements each). Average result±SD is shown *, $p<0.001$ FIGS. 9A–B. Induction of fetal gene expression in MEK5DD-transgenic hearts. RNA was prepared from wild-type and transgenic hearts.

Sectioning of transgenic hearts revealed that the walls of both the right and left ventricular chambers were extremely thin relative to wild-type (FIG. 7B). Closer examination of sections revealed a decrease in cross-sectional area of myocytes in the hearts of 8 week-old MEK5DD-transgenic mice (FIGS. 8A, 8B and 8D). The decreased myocyte cross-sectional area observed in MEK5DD-transgenic hearts contrasts sharply with the dramatic increase in myocyte cross-sectional area in the hearts of mice that overexpress an activated form of the calcium-regulated phosphatase, calcineurin, in the heart (FIGS. 8A and 8C) (Molkentin et al., 1998).

Average cross-sectional areas of cardiac myocytes from MEK5DD-transgenic and wild-type mice were determined at 1, 2, and 3 weeks of age. At 1 and 2 weeks of age, myocyte cross-sectional area was not significantly different between transgenic and control; however, by 3 weeks of age average myocyte cross-sectional area was decreased by 12% in MEK5DD-transgenic hearts relative to wild-type (data not shown). Cross-sectional area of cardiac myocytes in wild-type hearts increased as mice aged, whereas cross-sectional area of cardiac myocytes from transgenic mice increased very little with age, with the result that cross-sectional area of cardiac myocytes in 8 week-old transgenic hearts was 44% less than control (FIG. 8D). Heart weight/tibia length ratios of MEK5DD-transgenic mice were not significantly different from wild-type animals (data not shown). The fact that MEK5DD-transgenic and wild-type hearts were similar in mass, despite significantly decreased myocyte cross-sectional area, suggests that myocytes in MEK5DD-transgenic hearts undergo growth by eccentric hypertrophy. Aside from the abnormal hypertrophy of cardiomyocytes, MEK5DD-transgenic hearts seemed remarkably healthy. Trichrome staining did not reveal any evidence of fibrosis and TUNEL assay did not indicate that levels of apoptosis were elevated even in severely dilated MEK5DD-hearts compared to wild-type hearts.

Functional Analysis of Transgenic Mice

The inventors hypothesized that the eccentric hypertrophy of MEK5DD-transgenic hearts resulted in decreased cardiac performance and eventually congestive heart failure. Indeed, transthoracic echocardiography showed significant left ventricular dilation, as assessed by the end diastolic diameter (LVED), at 6 and 10 weeks of age compared to wild-type controls (Table 5). In addition, septal and posterior wall thickness was reduced compared to wild-type (Table 5). These measurements indicate a phenotype of primary dilated cardiomyopathy without ventricular hypertrophy. Furthermore, at 6 weeks of age, MEK5DD-transgenic hearts displayed a highly significant reduction of fractional shortening (Table 5). This reduction was even more pronounced at 10 weeks of age, indicating a progressive worsening of ventricular function. These data suggest that cardiac failure due to dilated cardiomyopathy may be the cause of death in MEK5DD-transgenic animals. Alternatively, severe arrhythmias could have resulted in the sudden death of transgenic animals.

TABLE 5

Echocardiography of MEK5DD-transgenic mice demonstrates eccentric hypertrophy and decreased fractional shortening

|  | Non-transgenic | MEK5DD-TG | % change |
| --- | --- | --- | --- |
| 6 weeks |  |  |  |
| IVSD | 0.67 ± 0.01 | 0.66 ± 0.004 | −1 |
| IVSS | 1.31 ± 0.01 | 1.04 ± 0.01 | −21** |
| LVPWD | 0.65 ± 0.01 | 0.60 ± 0.01 | −5 |
| LVPWS | 1.08 ± 0.02 | 0.90 ± 0.01 | −17 |
| LVED | 3.57 ± 0.03 | 4.47 ± 0.06 | +28* |
| LVES | 1.92 ± 0.02 | 3.39 ± 0.07 | +76** |
| FS | 0.46 ± 0.04 | 0.25 ± 0.06 | −47** |

TABLE 5-continued

Echocardiography of MEK5DD-transgenic mice demonstrates eccentric hypertrophy and decreased fractional shortening

|  | Non-transgenic | MEK5DD-TG | % change |
|---|---|---|---|
| 10 weeks |  |  |  |
| IVSD | 0.61 ± 0.004 | 0.57 ± 0.003 | −4 |
| IVSS | 1.15 ± 0.01 | 0.91 ± 0.01 | −21* |
| LVPWD | 0.59 ± 0.01 | 0.54 ± 0.01 | −5 |
| LVPWS | 1.08 ± 0.01 | 0.77 ± 0.01 | −29** |
| LVED | 3.85 ± 0.04 | 5.58 ± 0.08 | +45** |
| LVES | 2.31 ± 0.05 | 4.65 ± 0.09 | +101** |
| FS | 0.41 ± 0.06 | 0.17 ± 0.06 | −58** |

Measurements are given in millimeters, except fractional shortening (FS), which is unitless. Values were determined from three separate M-mode measurements and averaged between six mice in the non-transgenic group and ten mice in the transgenic group. Values are mean ± SEM;
*, $p < 0.05$;
** $p < 0.001$.
IVSD, interventricular septum diastole;
IVSS, interventricular septum systole;
LVPWD, left ventricular posterior wall diastole;
LVPWS, left ventricular posterior wall systole;
LVED, left ventricular end diastolic dimension;
LVES left ventricular end systolic dimension.

Induction of Fetal Gene Expression in MEK5DD-Transgenic Hearts

Figure 9:
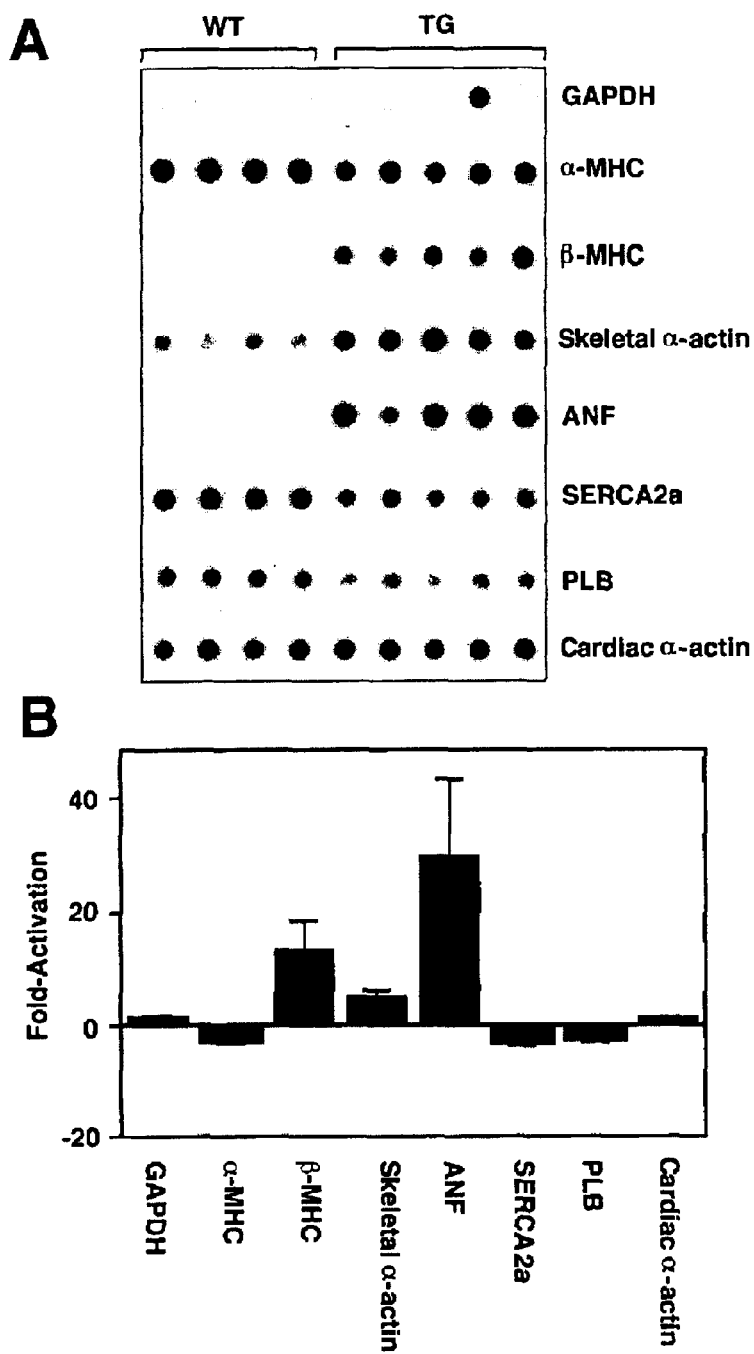
(FIG. 9A) RNA dot blots were prepared with 1 ug of RNA/dot and probed with an oligonucleotide probes specific for the indicated gene.
(FIG. 9B) The average -fold induction or repression of gene expression±SD for MEK5DD-transgenic animals relative to wild-type is shown. Signal intensity was quantitated using a Phosphor Imager.

To determine if MEK5DD-transgenic hearts showed stress-associated patterns of gene expression, the inventor performed dot blot analysis on RNA extracted from hearts of 8 week-old wild-type and transgenic animals (FIG. 9A). α-MHC, sarcoplasmic reticulum calcium ATPase-2a (SERCA2a), and phospholamban (PLB), which are typically down-regulated in failing hearts, were all down-regulated in hearts from MEK5DD-transgenics (FIG. 9B). Conversely, β-MHC, skeletal α-actin, and ANF, which are typically induced during heart failure, were upregulated by 12-, 5-, and 30-fold, respectively, in MEK5DD-transgenic hearts (FIG. 9B).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

XI. References

The following references, to the extent that they provide exemplary procedural or other details supplementary to those set forth herein, are specifically incorporated herein by reference:

U.S. Pat. No. 4,196,265
U.S. Pat. No. 4,554,101
U.S. Pat. No. 4,873,191
U.S. Pat. No. 4,879,236
U.S. Pat. No. 5,354,855
U.S. Pat. No. 5,792,453
U.S. Pat. No. 5,871,986
U.S. Pat. No. 6,100,242
Abe et al., Circ. Res., 86, 607–9, 2000.
Abe et al., J. Biol. Chem., 271, 16586–90, 1996.
Adams et al., Proc. Nat'l Acad. Sci. USA, 95, 10140–45, 1998.
Angel et al., Mol. Cell. Biol., 7:2256, 1987.
Angel et al., Mol. Cell. Biol., 7:2256, 1987a.
Angel et al., Cell, 49:729, 1987b.
Atchison and Perry, Cell, 48:121, 1987.
Atchison and Perry, Cell, 46:253, 1986.
Ausubel et al., In: Current Protocols in Molecular Biology, John, Wiley and Sons, Inc., 1994.
Baichwal and Sugden, In: Gene Transfer, Kucherlapati R, ed., New York, Plenum Press, pp. 117–148, 1986.
Banerji et al., Cell, 27(2 Pt 1):299–308, 1981.
Banerji et al., Cell, 33(3):729–740, 1983.
Barany and Merrifield, In: The Peptides, Gross and Meienhofer, eds., Academic Press, New York, pp. 1–284, 1979.
Barnes et al., J Biol Chem, 272(17):11510–7, 1997.
Becker et al., Meth. Cell Biol., 43, 161–89, 1994.
Benvenisty and Neshif, Proc. Nat'l Acad. Sci. USA 83(24):9551–9555, 1986.
Berkhout et al., Cell, 59:273–282, 1989.
Bhavsar P K, Brand N J, Yacoub M H, Barton P J R, Genomics, 35(1):11–23, 1996.
Blanar et al., EMBO J., 8:1139, 1989.
Bodine and Ley, EMBO J., 6:2997, 1987.
Boshart et al., Cell, 41:521, 1985.
Bosze et al., EMBO J., 5(7):1615–1623, 1986.
Braddock et al., Cell, 58:269, 1989.
Brinster et al., Proc. Nat'l Acad. Sci. USA, 82: 4438–4442, 1985.
Bueno et al., Circ. Res., 88, 88–96, 2001.
Bueno et al., EMBO J., 19, 6341–6350, 2000.
Bulla and Siddiqui, J. Virol., 62:1437, 1986.
Campbell and Villarreal., Mol. Cell. Biol., 8:1993, 1988.
Campere and Tilghman, Genes and Dev., 3:537, 1989.
Campo et al., Nature, 303:77, 1983.
Capaldi et al., Biochem. Biophys. Res. Comm., 76:425, 1977
Celander and Haseltine, J. Virology, 61:269, 1987.
Celander et al., J. Virology, 62:1314, 1988.
Chandler et al., Cell, 33:489, 1983.
Chang et al., Mol. Cell. Biol., 9:2153, 1989.
Chang et al., Hepatology, 14:134A, 1991.
Chatterjee et al., Proc Natl. Acad Sci. U.S.A., 86:9114, 1989.
Chen and Okayama, Mol. Cell Biol., 7(8):2745–2752, 1987.
Chien, Cell, 98, 555–8, 1999.
Choi et al., Cell, 53:519, 1988.
Coffin, Retroviridae and Their Replication. In: Virology, Fields et al., eds., Raven Press, New York, pp. 1437–1500, 1990.
Cohen et al., J. Cell. Physiol., 5:75, 1987.
Cook et al., Cell, 27:487–496, 1981.
Costa et al., Mol. Cell. Biol., 8:81, 1988.
Couch et al., Am. Rev. Resp. Dis., 88:394–403, 1963.
Coupar et al., Gene, 68:1–10, 1988.
Cowley et al., Cell 77:841–852, 1994.
Cripe et al., EMBO J., 6:3745, 1987.
Culotta and Hamer, Mol. Cell. Biol., 9:1376, 1989.
Dandolo et al., J. Virology, 47:55–64, 1983.
De Villiers et al., Nature, 312(5991):242–246, 1984.
Deschamps et al., Science, 230:1174–1177, 1985.
Dubensky et al., Proc. Nat'l Acad. Sci. USA, 81:7529–7533, 1984.
Edbrooke et al., Mol. Cell. Biol., 9:1908, 1989.

Edlund et al., *Science*, 230:912–916, 1985.
English et al., *Exper. Cell Res.*, 253, 255–70, 1999a.
English et al., *J. Biol. Chem.*, 274, 31588–92, 1999b.
English et al., *J. Biol. Chem.*, 270(48):28897–28902, 1995.
EPO Patent No. 0273085
Fechheimer et al., *Proc. Nat'l Acad. Sci. USA*, 84:8463–8467, 1987.
Feng and Holland, *Nature*, 334:6178, 1988.
Fentzke et al., *J. Clin. Invest.*, 101, 2415–26, 1998.
Ferkol et al., *FASEB J.*, 7:1081–1091, 1993.
Firak and Subramanian, *Mol. Cell. Biol.*, 6:3667, 1986.
Foecking and Hofstetter, *Gene*, 45(1):101–105, 1986.
Forster & Symons, *Cell*, 49:211–220, 1987.
Fraley et al., *Proc. Nat'l Acad. Sci. USA*, 76:3348–3352, 1979.
Franz W M, et al., *Cardioscience*, 5(4):235–43, 1994.
Frey et al., *Nature Med.*, 6, 1221–1227, 2000.
Friedmann, *Science*, 244:1275–1281, 1989.
Fujita et al., *Cell*, 49:357, 1987.
Fukuhara et al., *J. Biol. Chem.*, 275, 21730–6, 2000.
Gerlach et al., *Nature (London)*, 328:802–805, 1987.
Ghosh and Bachhawat, In: *Liver Diseases, Targeted Diagnosis and Therapy Using Specific Receptors and Ligands*. Wu et al., eds., Marcel Dekker, New York, pp. 87–104, 1991.
Ghosh-Choudhury et al., *EMBO J.*, 6:1733–1739, 1987.
Gilles et al., *Cell*, 33:717, 1983.
Gloss et al., *EMBO J.*, 6:3735, 1987.
Godbout et al., *Mol. Cell. Biol*, 8:1169, 1988.
Goding, In: *Monoclonal Antibodies: Principles and Practice*, 2d ed., Academic Press, Orlando, Fla., pp. 60–61, and 71–74, 1986.
Gomez-Foix et al., *J. Biol. Chem.*, 267:25129–25134, 1992.
Goodbourn and Maniatis, *Proc. Nat'l Acad. Sci. USA*, 85:1447, 1988.
Goodbourn et al., *Cell*, 45:601, 1986.
Gopal., *Mol. Cell Biol.*, 5:1188–1190, 1985.
Gopal-Srivastava et al., *Mol Cell Biol* 15(12):7081–90, 1995.
Gorman, et al., *Proc Nat'l Acad. Sci. (USA)*, 1982; 79(22):6777–81, 1982.
Graham and Prevec, In: *Methods in Molecular Biology: Gene Transfer and Expression Protocol*, E. J. Murray, ed., Humana Press, Clifton, N.J., 7:109–128, 1991.
Graham and van der Eb, *Virology*, 52:456–467, 1973.
Graham, et. al., *J. Gen. Virl.*, 36(1):59–74, 1977.
Greene et al., *Immunology Today*, 10:272, 1989
Grosschedl and Baltimore, *Cell*, 41:885, 1985.
Grunhaus and Horwitz, *Seminar in Virology*, 3:237–252, 1992.
Gulick et al., *J. Biol. Chem.*, 266, 9180–5, 1991.
Guzman, et al., *Circulation*, 88(6):2838–48, 1993.
Hammond, et al., *Clin. Res.* 42:123A, 1994.
Harland and Weintraub, *J. Cell Biol.*, 101:1094–1099, 1985.
Harlow and Lane, Antibodies: A Laboratory manual., Cold Spring Harbor Laboratory, 1988.
Haslinger and Karin, *Proc. Nat'l Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Nat. Acad. Sci. USA*, 81:6466–6470, 1984.
Herr and Clarke, *Cell*, 45:461, 1986.
Hersdorffer et al., *DNA Cell Biol.*, 9:713–723, 1990.
Herz and Gerard, *Proc. Nat'l Acad. Sci. USA*, 90:2812–2816, 1993.
Hidaka, et. al., *J. Clin. Invest.* 103(4):549–587, 1999.
Hirochika et al., *J. Virol.*, 61:2599, 1987.
Hirsch et al., *Mol. Cell. Biol.*, 10:1959, 1990.
Hogan et al., In: *Manipulating the Mouse Embryo*: A Laboratory Manual., 2nd ed., Cold Spring Harbor Laboratory Press, 1994.
Holbrook et al., *Virology*, 157:211, 1987.
Horlick and Benfield, *Mol. Cell. Biol.*, 9:2396, 1989.
Horwich, et al., *J. Virol.*, 64:642–650, 1990.
Huang et al., *Cell*, 27:245, 1981.
Hug et al., *Mol. Cell. Biol.*, 8:3065, 1988.
Hwang et al., *Mol. Cell. Biol.*, 10:585, 1990.
Ikeda and Ross, *Curr. Opin. Card.*, 15, 197–201, 2000.
Imagawa et al., *Cell*, 51:251, 1987.
Imbra and Karin, *Nature*, 323:555, 1986.
Imler et al., *Mol. Cell. Biol*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Johnson et al., In: *Biotechnology And Pharmacy*, Pezzuto et al., eds., Chapman and Hall, New York, 1993.
Jones and Shenk, *Cell*, 13:181–188, 1978.
Jones et al., *J. Clin. Inv.*, 98:1906–17, 1996.
Joyce, *Nature*, 338:217–244, 1989.
Kadesch and Berg, *Mol. Cell. Biol.*, 6:2593, 1986.
Kamakura et al., *J. Biol. Chem.*, 274, 26563–71, 1999.
Kaneda et al., *Science*, 243:375–378, 1989.
Karin et al., *Mol. Cell. Biol.*, 7:606, 1987.
Karin et al., *Mol. Cell. Biol.*, 7:606, 1987.
Karlsson et al., *EMBO J.*, 5:2377–2385, 1986.
Kasler et al., *Mol. Cell. Biol.*, 20, 8382–8389, 2000.
Katinka et al., *Cell*, 20:393, 1980.
Kato et al., *J. Biol. Chem.*, 266:3361–3364, 1991.
Kato et al., *Circ. Res.*, 87:937–945, 2000.
Kato et al., *EMBO*, 16(23):7054–7066, 1997.
Kawamoto et al., *Mol. Cell. Biol.*, 8:267, 1988.
Kelly et al., *J Cell Biol*, 129(2):383–96, 1995.
Kiledjian et al., *Mol. Cell. Biol.*, 8:145, 1988.
Kim & Cook, *Proc. Nat'l Acad. Sci. USA*, 84:8788–8792, 1987.
Kimura S, et al, *Dev Growth Differ.* 39(3):257–65, 1997.
Klamut et al., *Mol. Cell. Biol.*, 10: 193, 1990.
Klein et al., *Nature*, 327:70–73, 1987.
Klesse et al., *Oncogene*, 18, 2055–68, 1999.
Koch et al., *Mol. Cell. Biol.*, 9:303, 1989.
Kodama et al., *Am. J. Phys.-Heart and Circ. Phys.*, 279, H1635-H1644, 2000.
Kriegler and Botchan, In: *Eukaryotic Viral Vectors*, Y. Gluzman, ed., Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunisada et al., *Circ*, 94:2626–32, 1996.
Kunz et al., *Nucl. Acids Res.*, 17:1121, 1989.
Kyte and Doolittle, *J. Mol. Biol.*, 157(1):105–132, 1982.
LaPointe et al., *Hypertension* 27(3 Pt 2):715–22, 1996.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Le Gal La Salle et al., *Science*, 259:988–990, 1993.
Lee et al., *Nature*, 294:228, 1981.
Lee et al., *Nucleic Acids Res.*, 12:4191–206, 1984.
Lee et al., *Bioch. & Biophys. Res. Comm.*, 213, 715–24, 1995.

Levinson et al., *Nature*, 295:79, 1982.
Levrero et al., *Gene*, 101: 195–202, 1991.
Lin et al., *Mol. Cell. Biol.*, 10:850, 1990.
Luria et al., *EMBO J.*, 6:3307, 1987.
Lusky and Botchan, *Proc Natl. Acad. Sci. U.S.A.*, 83:3609, 1986.
Lusky et al., *Mol. Cell. Biol.* 3:1108, 1983.
Macejak and Sarnow, *Nature*, 353:90–94, 1991.
MacLellan et al., *Circ. Res.*, 81, 137–44, 1997.
Majors and Varmus, *Proc. Nat'l Acad. Sci. USA*, 80:5866, 1983.
Mann et al., *Cell*, 33:153–159, 1983.
Mansour et al., *Science*, 265:966–970, 1994.
Markowitz et al., *J. Virol.*, 62:1120–1124, 1988.
McNeall et al., *Gene*, 76:81, 1989.
Merrifield, *Science*, 232: 341–347, 1986.
Michel and Westhof, *J. Mol. Biol.*, 216:585–610, 1990.
Miksicek et al., *Cell*, 46:203, 1986.
Milner et al., *J. Mol. & Cell. Card.*, 31, 2063–76, 1999.
Molkentin et al., *Cell*, 93, 215–28, 1998.
Mordacq and Linzer, *Genes and Dev.*, 3:760, 1989.
Moreau et al., *Nucl. Acids Res.*, 9:6047, 1981.
Moss et al., *J Biol Chem*, 271(49):31688–94, 1996.
Muesing et al., *Cell*, 48:691, 1987.
Ng et al., *Nuc. Acids Res.*, 17:601, 1989.
Nicol et al., EMBO 20 (11) 1–11, 2001.
Nicol et al., *Ann. Rev. Gen. Gen.*, 1, 179–223, 2000.
Nicolas and Rubinstein, In: *Vectors: A survey of molecular cloning vectors and their uses*, Rodriguez and Denhardt, eds., Stoneham: Butterworth, pp. 494–513, 1988.
Nicolau and Sene, *Biochim. Biophys. Acta*, 721:185–190, 1982.
Nicolau et al., *Methods Enzymol.*, 149:157–176, 1987.
Oh et al., *J. Biol. Chem.*, 273:9703–10, 1998.
Ondek et al., *EMBO J.*, 6:1017,1987.
Ornitz et al., *Mol. Cell Biol.*, 7:3466, 1987.
Palmiter et al., *Nature*, 300:611, 1982.
Palmiter et al., *Nature*, 300:611, 1982.
Paskind et al., *Virology*, 67:242–248, 1975.
Passier et al., *J. Clin. Invest.*, 105, 1395–406, 2000.
Pech et al., *Mol. Cell. Biol.*, 9:396, 1989.
Pelletier and Sonenberg, *Nature*, 334:320–325, 1988.
Perales et al., *Proc. Nat'l Acad. Sci.* 91:4086–4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Nat'l Acad. Sci. USA*, 82:1020, 1985.
Porton et al., *Mol. Cell. Biol.*, 10:1076, 1990.
Potter et. al., *Proc. Nat'l Acad. Sci. USA*, 81:7161–7165, 1984.
Queen and Baltimore, *Cell*, 35:741, 1983.
Quinn et al., *Mol. Cell. Biol.*, 9:4713, 1989.
Racher et al., *Biotechnology Techniques*, 9:169–174, 1995.
Ragot et al., *Nature*, 361:647–650, 1993.
Redondo et al., *Science*, 247:1225, 1990.
Reinhold-Hurek & Shub, *Nature*, 357:173–176, 1992.
Reisman and Rotter, *Mol. Cell. Biol.*, 9:3571, 1989.
Remington's Pharmaceutical Science", 15$^{th}$ Ed., pg. 1035–1038 and 1570–1580.
Renan, *Radiother. Oncol.*, 19:197–218, 1990.
Resendez Jr. et al., *Mol. Cell. Biol.*, 8:4579, 1988.
Rich et al., *Hum. Gene Ther.*, 4:461–476, 1993.
Ridgeway, In: *Vectors: A Survey of Molecular Cloning Vectors and Their Uses*, Rodriguez et al., eds., Stoneham: Butterworth, pp. 467–492, 1988.
Ripe et al., *Mol. Cell. Biol.*, 9:2224, 1989.
Rippe et al., *Mol. Cell Biol.*, 10:689–695, 1990.
Ritchie, M. E., *J. Biol. Chem.* 271(41):25485–25491, 1996.
Rittling et al., *Nuc. Acids Res.*, 17:1619, 1989.
Rosen et al., *Cell*, 41:813, 1988.
Rosenfeld et al., *Cell*, 68:143–155, 1992.
Rosenfeld et al., *Science*, 252:431–434, 1991.
Roux et al., *Proc. Nat'l Acad. Sci. USA*, 86:9079–9083, 1989.
Ruwhof and van der Laarse, *Card. Res.*, 47, 23–37, 2000.
Sakai et al., *Genes and Dev.*, 2:1144, 1988.
Sambrook et. al., In: *Molecular Cloning: A Laboratory Manual*, 2d Ed., Cold Spring Harbor Laboratory Press, Cold Spring Harbor, N.Y., 1989.
Sarver, et al., *Science*, 247:1222–1225, 1990.
Satake et al., *J. Virology*, 62:970, 1988.
Scanlon et. al., *Proc. Nat'l Acad. Sci. USA*, 88:10591–10595, 1991.
Schaffner et al., *J. Mol. Biol.*, 201:81, 1988.
Schiaffino and Reggiani, *Physiol. Rev.*, 76:371–423, 1996.
Searle et al., *Mol. Cell. Biol.*, 5:1480, 1985.
Seger et al., *J. Biol. Chem.* 269:25699–25709, 1994.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stewart and Young, *Solid Phase Peptide Synthesis*, 2d. ed., Pierce Chemical Co., 1984.
Stratford-Perricaudet and Perricaudet, In: *Human Gene Transfer*, O. Cohen-Haguenauer et al., eds., John Libbey Eurotext, France, pp. 51–61, 1991.
Stratford-Perricaudet et al, *Hum. Gene. Ther.*, 1:241–256, 1990.
Stuart et al., *Nature*, 317:828, 1985.
Sugden and Clerk, *Circ. Res.*, 83: 345–352, 1998.
Sugden and Clerk, *J. Mol. Med.*, 76:725–46, 1998.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Takeishi et al., *Circ. Res.*, 85:1164–72, 1999.
Tam et al., *J. Am. Chem. Soc.*, 105:6442, 1983.
Tamura et al., *J. Mol. & Cell. Card.*, 30:2175–81, 1998.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati ed., New York, Plenum Press, pp. 149–188, 1986.
Thiesen et al., *J. Virology*, 62:614, 1988.
Top et. al., *J. Infect. Dis.*, 124:155–160, 1971.
Treisman, *Cell*, 42:889, 1985.
Tronche et al., *Mol. Biol. Med.*, 7:173, 1990.
Trudel and Constantini, *Genes and Dev.* 6:954, 1987.
Tur-Kaspa et al., *Mol. Cell Biol.*, 6:716–718, 1986.
Tyndell et al., *Nuc. Acids. Res.*, 9:6231, 1981.
Uetsuki, et al., *J. Biol. Chem.*, 264(10):5791–5798 (1989).
Vannice and Levinson, *J. Virology*, 62:1305, 1988.
Varmus et al., *Cell*, 25:23–36, 1981.
Vasseur et al., *Proc Natl. Acad. Sci. U.S.A.*, 77:1068, 1980.
Wagner et al., *Proc. Nat'l Acad. Sci. USA* 87(9):3410–3414, 1990.
Wakabayashi-Ito, et al., *J. Biol. Chem.*, 269(47):29831–29837, 1994.

Wang and Calame, *Cell,* 47:241, 1986.
Wang et al., *J. Biol. Chem.,* 273, 2161–8, 1998a.
Wang et al., *J. Biol. Chem.,* 273, 5423–6, 1998b.
Weber et al., *Cell,* 36:983, 1984.
Weinberger et al. *Mol. Cell. Biol.,* 8:988, 1984.
Winoto and Baltimore, *Cell* 59:649, 1989.
WO Patent No. 84/03564
Wollert and Chien, *J. Mol. Med.,* 75, 492–501, 1997.
Wollert et al. *J. Biol. Chem.,* 271, 9535–45, 1997.
Wong et al., *Gene,* 10:87–94, 1980.
Wu and Wu, *Adv. Drug Delivery Rev.,* 12:159–167, 1993.
Wu and Wu, *Biochemistry,* 27:887–892, 1988.
Wu and Wu, *J. Biol. Chem.,* 262:4429–4432, 1987.
Yamauchi-Takihara, et. al., *Proc. Nat'l Acad. Sci. USA* 86(10):3504–3508, 1989.
Yang et al., *Proc. Na't. Acad. Sci. USA,* 87:9568–9572, 1990.
Yutzey et al. *Mol. Cell. Biol.,* 9:1397, 1989.
Zelenin et al., *FEBS Lett.,* 280:94–96, 1991.
Zhang et al., *Nat. Med.* 6: 556–63, 2000.
Zhou et al. *J. Biol. Chem.,* 270(21) 12665–12669, 1995.
Ziober and Kramer, *J Biol Chem,* 271(37):22915–22, 1996.

What is claimed is:

1. A transgenic mouse, the genome of which comprises an exogenous nucleic acid encoding MEK5DD, operably linked to the alpha-myosin heavy chain promoter, wherein said MEK5DD is expressed in the heart cells of said mouse and wherein said mouse exhibits increased heart size, atrial enlargement, ventricular wall thinning, and eccentric hypertrophy, as compared to wild-type mice.

* * * * *

UNITED STATES PATENT AND TRADEMARK OFFICE
CERTIFICATE OF CORRECTION

PATENT NO. : 6,924,415 B2
DATED : August 2, 2005
INVENTOR(S) : Olson et al.

It is certified that error appears in the above-identified patent and that said Letters Patent is hereby corrected as shown below:

<u>Title page,</u>
Item [57], ABSTRACT,
Line 4, after "its role" insert -- in --.
Line 6, delete "decrease" insert -- decreased --.

Signed and Sealed this

Twenty-first Day of February, 2006

JON W. DUDAS
*Director of the United States Patent and Trademark Office*